(12) United States Patent
Brown et al.

(10) Patent No.: US 12,096,989 B2
(45) Date of Patent: Sep. 24, 2024

(54) PLAN IMPLEMENTATION

(71) Applicant: Biomet Manufacturing, LLC, Warsaw, IN (US)

(72) Inventors: David R. Brown, Warsaw, IN (US); Troy W. Hershberger, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 349 days.

(21) Appl. No.: 17/490,146

(22) Filed: Sep. 30, 2021

(65) Prior Publication Data
US 2022/0015833 A1   Jan. 20, 2022

Related U.S. Application Data

(63) Continuation of application No. 15/917,156, filed on Mar. 9, 2018, now Pat. No. 11,160,611, which is a
(Continued)

(51) Int. Cl.
A61B 34/10 (2016.01)
A61B 17/17 (2006.01)
(Continued)

(52) U.S. Cl.
CPC .......... *A61B 34/10* (2016.02); *A61B 17/1703* (2013.01); *A61B 17/1717* (2013.01);
(Continued)

(58) Field of Classification Search
CPC . A61B 34/10; A61B 17/1703; A61B 17/1717; A61B 17/1764; A61B 17/72; A61B 34/20; A61B 2017/00526; A61B 2034/101; A61B 2034/105; A61B 2034/107; A61B 2034/108; A61B 2034/2046; A61B 2034/2065; A61B 2034/2074; A61F 2/4607; A61F 2/4657;
(Continued)

(56) References Cited

U.S. PATENT DOCUMENTS 4,759,350 A   7/1988   Dunn et al.
5,228,459 A   7/1993   Caspari et al.
(Continued)

FOREIGN PATENT DOCUMENTS

CN   101534750 A   9/2009
CN   102695477 A   9/2012
(Continued)

OTHER PUBLICATIONS

"U.S. Appl. No. 14/594,409, Non Final Office Action mailed Jul. 26, 2017", 40 pgs.
(Continued)

*Primary Examiner* — Kandasamy Thangavelu
(74) *Attorney, Agent, or Firm* — SCHWEGMAN LUNDBERG & WOESSNER, P.A.

(57) ABSTRACT

A system and method for performing a procedure is disclosed. The procedure may include preparing one or more bones for a prosthetic implant. The method may include provide instructions to a user for using identified instruments to perform a procedure. Instructions and may be provided for settings of adjustable instruments.

16 Claims, 11 Drawing Sheets

Related U.S. Application Data continuation of application No. 14/594,409, filed on Jan. 12, 2015, now Pat. No. 9,931,168.

(51) Int. Cl.
  *A61B 17/72* (2006.01)
  *A61B 34/20* (2016.01)
  *A61F 2/46* (2006.01)
  *G06F 30/00* (2020.01)
  *A61B 17/00* (2006.01)
  *G16H 50/50* (2018.01)

(52) U.S. Cl.
  CPC .......... *A61B 17/1764* (2013.01); *A61B 17/72* (2013.01); *A61B 34/20* (2016.02); *A61F 2/4607* (2013.01); *A61F 2/4657* (2013.01); *G06F 30/00* (2020.01); *A61B 2017/00526* (2013.01); *A61B 2034/101* (2016.02); *A61B 2034/105* (2016.02); *A61B 2034/107* (2016.02); *A61B 2034/108* (2016.02); *A61B 2034/2046* (2016.02); *A61B 2034/2065* (2016.02); *A61B 2034/2074* (2016.02); *A61F 2002/4663* (2013.01); *A61F 2240/004* (2013.01); *G16H 50/50* (2018.01)

(58) Field of Classification Search
  CPC ....... A61F 2002/4663; A61F 2240/004; G06F 30/00; G16H 50/50
  See application file for complete search history.

(56) References Cited

U.S. PATENT DOCUMENTS

| | | | |
|---|---|---|---|
| 5,720,752 | A | 2/1998 | Elliott et al. |
| 5,743,915 | A | 4/1998 | Bertin et al. |
| 6,077,270 | A | 6/2000 | Katz |
| 9,931,168 | B2 | 4/2018 | Brown |
| 11,160,611 | B2 | 11/2021 | Brown et al. |
| 2001/0018589 | A1 | 8/2001 | Muller |
| 2005/0049603 | A1 | 3/2005 | Calton et al. |
| 2005/0054917 | A1 | 3/2005 | Kitson |
| 2006/0142774 | A1 | 6/2006 | Metzger |
| 2008/0058949 | A1 | 3/2008 | Dees et al. |
| 2008/0319448 | A1 | 12/2008 | Lavallee et al. |
| 2009/0005871 | A1 | 1/2009 | White et al. |
| 2009/0222014 | A1 | 9/2009 | Bojarski et al. |
| 2010/0063508 | A1 | 3/2010 | Borja et al. |
| 2010/0305575 | A1 | 12/2010 | Wilkinson et al. |
| 2011/0029093 | A1 | 2/2011 | Bojarski |
| 2011/0046685 | A1 | 2/2011 | Faure et al. |
| 2011/0071532 | A1* | 3/2011 | Carson .................. A61B 34/20 606/88 |
| 2011/0295378 | A1 | 12/2011 | Bojarski et al. |
| 2012/0041446 | A1 | 2/2012 | Wong et al. |
| 2012/0230573 | A1 | 9/2012 | Ito et al. |
| 2013/0085500 | A1 | 4/2013 | Meridew et al. |
| 2014/0188240 | A1* | 7/2014 | Lang ..................... A61F 2/3662 29/592 |
| 2014/0257309 | A1* | 9/2014 | Aram .................... A61F 2/3859 606/88 |
| 2014/0276240 | A1 | 9/2014 | Stein et al. |
| 2015/0182292 | A1 | 7/2015 | Hladio et al. |
| 2016/0045317 | A1 | 2/2016 | Lang et al. |
| 2016/0199134 | A1 | 7/2016 | Brown et al. |
| 2016/0287395 | A1 | 10/2016 | Khalili et al. |
| 2018/0235705 | A1 | 8/2018 | Brown et al. |

FOREIGN PATENT DOCUMENTS

| | | | | |
|---|---|---|---|---|
| CN | 103841924 | A | * 6/2014 | ........... A61B 17/155 |
| CN | 107427309 | A | 12/2017 | |
| WO | WO 2005087125 | A2 | * 9/2005 | ........... A61B 6/4266 |
| WO | WO 2006129087 | A1 | * 12/2006 | ............. A61B 90/36 |
| WO | WO 2008112996 | A1 | * 9/2008 | ......... A61B 17/1767 |
| WO | WO-2014145267 | A1 | 9/2014 | |
| WO | WO-2014153530 | A1 | 9/2014 | |
| WO | WO-2016115019 | A2 | 7/2016 | |
| WO | WO-2016115019 | A3 | 7/2016 | |

OTHER PUBLICATIONS

"U.S. Appl. No. 14/594,409, Notice of Allowance mailed Nov. 27, 2017", 11 pgs.
"U.S. Appl. No. 14/594,409, Response filed Oct. 25, 2017 to Non Final Office Action mailed Jul. 26, 2017", 13 pgs.
"U.S. Appl. No. 15/917,156, Final Office Action mailed Apr. 21, 2021", 19 pgs.
"U.S. Appl. No. 15/917,156, Non Final Office Action mailed Jan. 11, 2021", 19 pgs.
"U.S. Appl. No. 15/917,156, Non Final Office Action mailed Jun. 11, 2020", 34 pgs.
"U.S. Appl. No. 15/917,156, Notice of Allowance mailed Jun. 30, 2021", 13 pgs.
"U.S. Appl. No. 15/917,156, Notice of Allowance mailed Oct. 15, 2020", 11 pgs.
"U.S. Appl. No. 15/917,156, Preliminary Amendment filed May 15, 2018", 7 pgs.
"U.S. Appl. No. 15/917,156, Response filed Apr. 12, 2021 to Non Final Office Action mailed Jan. 11, 2021", 10 pgs.
"U.S. Appl. No. 15/917,156, Response filed Jun. 21, 2021 to Final Office Action mailed Apr. 21, 2021", 11 pgs.
"U.S. Appl. No. 15/917,156, Response filed Sep. 11, 2020 to Non Final Office Action mailed Jun. 11, 2020", 12 pgs.
"Canadian Application Serial No. 2,973,699, Office Action mailed Apr. 11, 2018", 4 pgs.
"Canadian Application Serial No. 2,973,699, Response filed Oct. 11, 2018 to Office Action mailed Apr. 11, 2018", 8 pgs.
"Chinese Application Serial No. 201680014965.3, Office Action mailed Jun. 28, 2018", w/ English translation, 12 pgs.
"Chinese Application Serial No. 201680014965.3, Office Action mailed Dec. 4, 2018", w/ English translation, 6 pgs.
"Chinese Application Serial No. 201680014965.3, Response filed Feb. 14, 2019 to Office Action mailed Dec. 4, 2018", w/English Claims, 6 pgs.
"Chinese Application Serial No. 201680014965.3, Response filed Oct. 10, 2018 to Office Action mailed Jun. 28, 2018", w/ English claims, 11 pgs.
"European Application Serial No. 16704077.3, Communication Pursuant to Article 94(3) EPC mailed Jun. 8, 2018", 5 pgs.
"European Application Serial No. 16704077.3, Response filed Mar. 19, 2018 to Office Action mailed Sep. 8, 2018", 15 pgs.
"European Application Serial No. 16704077.3, Response filed Oct. 18, 2018 to Communication Pursuant to Article 94(3) EPC mailed Jun. 8, 2018", 18 pgs.
"International Application Serial No. PCT/US2016/012816, International Preliminary Report on Patentability mailed Jul. 27, 2017", 11 pgs.
"International Application Serial No. PCT/US2016/012816, International Search Report mailed Aug. 4, 2016", 7 pgs.
"International Application Serial No. PCT/US2016/012816, Invitation to Pay Additional Fees and Partial Search Report mailed May 17, 2016", 6 pgs.
"International Application Serial No. PCT/US2016/012816, Written Opinion mailed Aug. 4, 2016", 9 pgs.
"Microplasty® Elite Total Knee Instrumentation", Surgical Technique Vanguard Complete Knee S stem. Biomet brochure, (2014), 37 pgs.
"Vanguard XP Total Knee System", Surgical Technique Biomet brochure 1-36, (2014), 38 pgs.

* cited by examiner

PLAN IMPLEMENTATION

FIELD

The subject disclosure relates to a system for performing a procedure, and particularly to a system for providing instructions, directions, or both for performing a procedure based upon a plan.

BACKGROUND

This section provides background information related to the present disclosure which is not necessarily prior art.

When performing a procedure, a user, such as a surgeon, can obtain access to a portion of the subject for various purposes. For example, a surgeon may incise tissue and resect a portion of bone for placing a prosthesis. The prosthesis is generally positioned based upon knowledge and practice of the surgeon after viewing the anatomical portions of the patient.

SUMMARY

This section provides a general summary of the disclosure, and is not a comprehensive disclosure of its full scope or all of its features.

Preparing for a procedure may include planning and identifying various features and landmarks in a structure. These landmarks may include anatomical landmarks in a subject, such as a human or animal patient. It is understood, however, that landmarks can include any internal structures or any structures on any appropriate subject, such as non-human or non-animal subjects. Specific examples include components within a case, such as within a shipping container, a fuselage of an aircraft, etc. Nevertheless, planning can be performed to identify a proposed positioning of various members and procedures to occur to achieve a selected result.

In various embodiments, a procedure on an anatomy can include positioning of a prosthesis in a human subject. In positioning a prosthesis in a human subject, the anatomy of the human subject may be altered. According to various embodiments, incisions may be made to obtain access to anatomical structures, such as boney portions, internal organs, and the like. During obtaining access to various anatomical portions, however, surface tissue and structures, such as adipose tissue, muscle, and skin, may interfere with complete visualization of various anatomical structures. Therefore, the use of image data that is acquired or analyzed prior to a procedure to plan a procedure may be helpful.

In preparing for a procedure, anatomical images may be acquired of a subject. The images may be studied and analyzed to determine a selected orientation and positioning of components to achieve a result for a subject. For example, a selected or determined appropriate position for a prosthesis may be made based upon an analysis of image data of a subject. After identifying a selected or determined location to achieve a selected result, a plan can be made or determined to achieve the selected or determined location. The plan may include positions of prosthetic members, positions of resection planes and resection amounts, and other specific features. This determined plan may direct a user or identify to a user settings for instruments to achieve the selected result based on positioning of various prosthetic members and/or resections.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
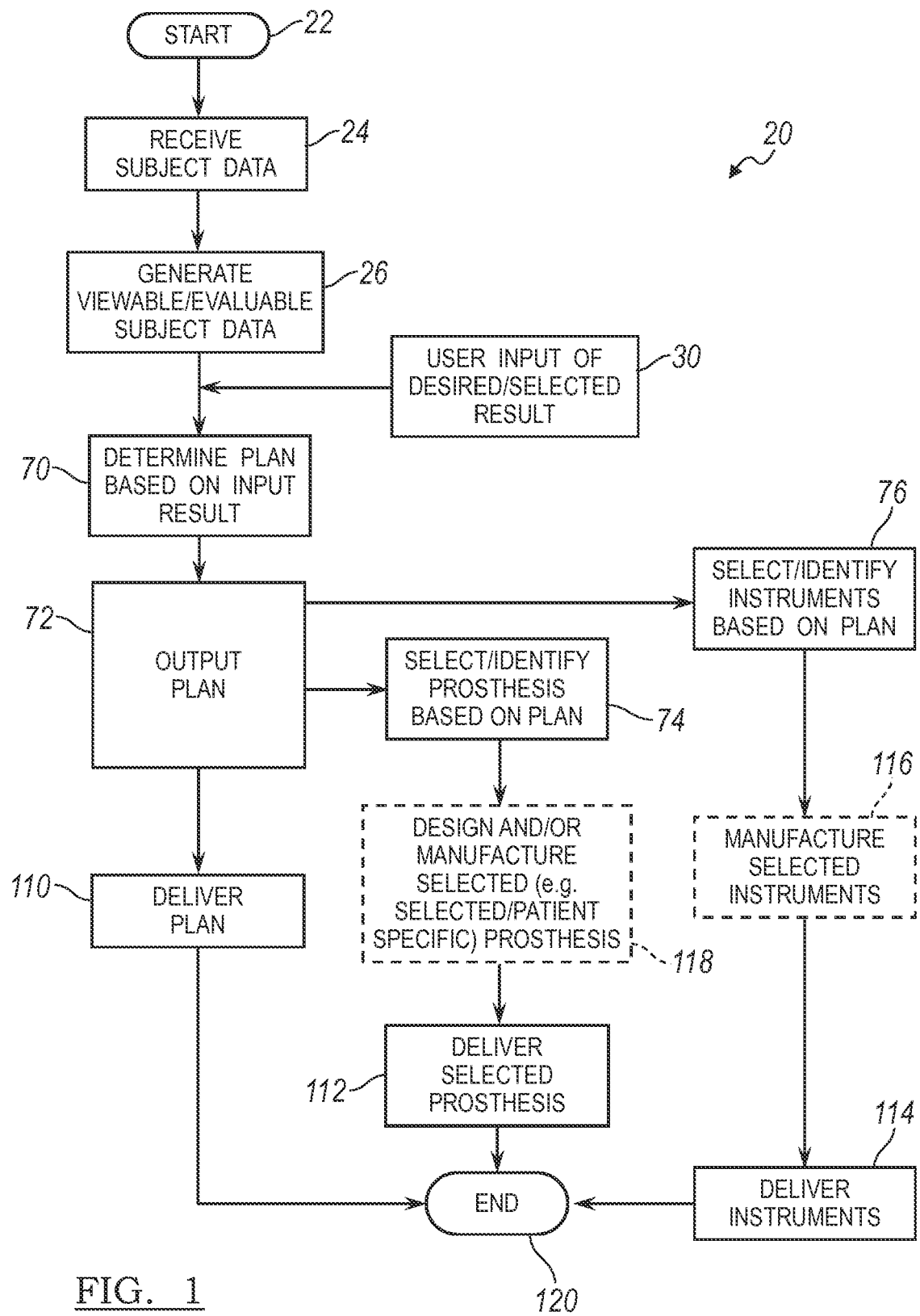
FIG. 1 is a flowchart illustrating a method of determining and providing a plan for a procedure.

Example embodiments will now be described more fully with reference to the accompanying drawings.

A plan, as discussed further herein, can be determined and prepared based upon selected data acquired regarding a subject. The data acquired of the subject can include image data acquired from various sources and using various techniques. The image data acquired from various sources can include two dimensional data or three dimensional data. For example, three dimensional image data can be acquired using magnetic resonances imaging (MRI) or computed tomography (CT) imaging. Additionally, a three-dimensional model can be reconstructed based upon various known reconstruction techniques using selected two dimensional images. For example, two substantially orthogonal images can be used to reconstruct a three dimensional (3D) model of a portion of a subject. The 3D reconstruction may created utilizing various software programs such as MIM-ICS® computer software sold by Materialise N.V. a company in BELGIUM or Amira™ computer software sold by FEI. The software programs are instructions of an algorithm that are executed by a selected processing or processor system. It is understood that the processor system may include circuits, application specific integrated circuit systems (ASICs), and/or general processor integrated circuits executing selected instructions, such as a central processor sold by, Intel, Inc.

Plans for procedures can be prepared for various selected anatomical portions. For example, a total hip arthroplasty (THA) can be performed on a subject. THA may include resection of a proximal femoral portion and an acetabulum followed by implantation of prosthetic members for a proximal femur and an acetabulum. Furthermore, total knee replacement, partial knee replacement, shoulder replacement and elbow replacement can also be further examples of prosthetic systems that are implanted into a patient. It is understood that total arthroplasty (generally understood to include replacement of two opposing portions of an articulating surface to completely replace the natural joint) and partial procedures (replacing less than a total articulating portion between two boney sections) can be performed. In various embodiments, a partial knee arthroplasty can include resection or replacement of a medial or lateral condyle of the femur either alone or in combination with a respective medial or lateral portion of the tibia. It is also understood that a partial hip arthroplasty can include resection or replacement of only one portion of a hip joint, such as resection or replacement of a femoral head and/or resection or replacement of an acetabulum or only selected portions of these portions of an anatomy. Similarly, complete or total replacement of any selected portion may be planned and/or performing, including of non-human or living subjects.

Nevertheless, an arthroplasty procedure can be planned using appropriate preparation information. As noted above, image data can be used to assist in determining a plan for performing a procedure. The plan can include selecting a final orientation of the anatomical portions, such as a placement and orientation of a femur relative to a pelvis, to achieve a selected outcome. For example, a varus or valgus angle can be selected to achieve a selected orientation of an anatomical portion and/or a range of motion of a joint after an implantation. Based upon the image data of a patient, the placement of various prosthetic components can be determined to achieve the selected varus or valgus angle. It is understood, however, that various other procedures can also be performed with a plan, as discussed further herein. For example, achieving a selected angle (which may also include a varus or valgus angle) of a tibia relative to a femur can be planned. Other anatomical orientations can also be planned for a subject.

As described in detail below, a process can include a program that may be executed with a processor (e.g. integrated circuit or application specific circuit) that is executing instructions based on stored software. A plan may then result in instructions that identify portions of an anatomy (or non-anatomical portions for a non-animal subject) and those portions of the anatomy are identified or localized to a subject. Once the location is identified on the subject according to the plan, an operating instrument, such as a drill or saw, may be positioned and stabilized relative to the identified portion to achieve the planned result.

Planning is done before actual implant placement is defined on the bone. It includes interactively determining where a final position of an implant is to be relative to patient specific landmarks. Landmarks may be identified during the plan, such as identifying landmarks (hard or soft tissue or axis, e.g. femoral epicondyles). The final position may include how an implant will be positioned to achieve selected and planned axes of patient bones, range-of-motion, and other selected results following implantation of a prosthesis. It may also include positioning of any appropriate or selected member relative to a subject or device. The plan may include various results (e.g. varus and valgus angle) based upon resection preparation that leads to prosthesis placement. The plan may be executed by a processor operating with selected software programs, including those discussed above. Further, the plan may be determined by evaluating a X-ray image and constructing a 2D template that may be used to identify landmarks and develop the plan.

During a procedure, such as placement and implantation of a prosthesis it may be desirable and/or necessary to identify on a bone the same datums or anatomic landmarks used in making and determining the plan. To ensure that a procedure, such as a resection, matches the plan, the landmarks identified or used by the plan may be identified during a procedure. These may include locating landmarks (hard or soft tissue or axis, e.g. femoral epicondyles). The landmarks may be used for proper resection and/or guide placement. Thus, during a procedure identifying and locating the landmarks may occur and may be referred to as localizing (registration) with the patient bone or other appropriate anatomy.

Once the landmarks are located, an instrument and/or guide, as discussed further herein, may be oriented or placed on and/or aligned with the landmarks. Positioning of an instrument may, therefore, occur based upon the plan. The landmarks identified, as noted above, may be used to orient an instrument, such as a drill or a cut guide, so that it facilitates shaping the bone to position the prosthesis consistent with the plan. Thus, the guides and instruments may be oriented based on the plan to achieve the selected results.

Stabilizing an instrument, such as a guide, during a procedure may also be selected and desirable. Stabilizing an instrument may be planned as a part of a stabilization plan. The stabilization plan may include identifying portions to contact with an instrument, forming or designing instrument portions for stabilization, etc. Further, the stabilization plan may be part of a plan formulated for a procedure, as discussed herein. For example, the instrument may be mounted so that it is precise, accurate, and stable. This may include having the instrument contact or be fixed to several points on a structure. For example, a guide may contact at least the medial and lateral femoral epicondyles in addition to an anterior point on a distal femur. All of the points of contact may be included as landmarks so that in stabilizing an instrument, it is also generally patient specific as well.

All of the identifying, stabilization, and positioning may be based on the plan. The plan may be based on information and data regarding a specific or single patient. Thus, the plan along with the identifying, stabilization, and positioning allow for and give a patient specific outcome.

In one example, such as distal femoral prosthetic placement, an IM rod may be one datum or landmark on the femur that both indicates an anatomic axis (IM canal) and generally provides a stable platform for an instrument in two axes. The IM rod can stabilize things in both a X and an Y axes, but not a Z (rotational) axis. Other landmarks may include the distal femoral posterior condyles which combined with the IM rod gives a rotational datum. The Z datum can be touching the most distal femoral condyle with a guide portion. Another datum may be an anterior cortex of the femur. For a tibia a datum may include an anterior face of the tibia or either side of the tibial tubercle. The width of the femur (or tibia) could also be used. It could be useful to check the articular cartilage low (thinnest) point, either tibial or distal femur. Once these datum are identified, the patient specific parameters from the plan can be applied relative to them. These datum allow the instruments to be positioned relative to the bone through the same datums as the plan, and then Stabilized such that they don't move. An instrument may also include patient specific portions or members, as discussed herein (including a stylus, a patient specific key or member, a patient specific setting, or a programmable or programmed portion that may alter an instrument to a specific setting) can be inserted into, attached to, or adjusted relative to other instrument portions to set guides in a Position to orient the implants identical to the Plan. Patient specific portions or settings can alternatively be applied prior to the other instrument portions being Positioned and Stabilized.

With reference to FIG. 1, a flowchart 20 illustrates a process for planning a procedure. It is understood that the planned procedure can be for any appropriate or selected portion of the anatomy, but the following discussion relates generally to a knee arthroplasty, which may include a complete knee arthroplasty. In a complete knee arthroplasty, a distal femur and a proximal tibia are resected and replaced with prosthetic components. The prosthetic components interact at the joint to reflect and/or mimic an optimal or selected anatomical interaction. This may include interaction with a pelvis at the hip joint as well.

Initially, the process illustrated in the flowchart 20 can begin at start block 22. It is understood that the method illustrated in the flowchart 20 can be incorporated into instructions that are executed by a processor system. The processor system can include a general purpose processor that is executing instructions that can be stored on a medium, such as a hard disk drive, network memory access, or other memory system. Further, the processor may be a specific processor, such as an application specific integrated circuit (ASIC). According to various embodiments, however, the method illustrated in the flowchart 20 can assist in providing an output for achieving a plan determined by input from a user, such as a surgeon, or based upon instructions within the system. The output may include, as discussed further herein, instrument portions, a list of components for a prosthesis system, and/or instructions to operate or incorporate the instrument or prosthetic portions into a procedure to achieve a planned result. Instructions may include settings for selected instruments, such as guides or sizers.

After the method is started in block 22, subject data can be received in block 24. Subject data can be any appropriate subject data such as three dimensional image data or two dimensional image data, or combinations thereof. For example, magnetic resonance images (MRI) that are used to generate three dimensional images of a subject may be incorporated or accessed. Further, or in addition to MRI data, computed tomography (CT) image data can be acquired. The CT image data may also be three dimensional image data that is analyzed or used in selecting a plan. Two dimensional image data can also be used to assist in creating a plan. According to various embodiments, two dimensional image data can be used to generate a three dimensional reconstruction based upon the two dimensional image data. A three dimensional reconstruction can be created with the software programs noted above. Further, a two dimensional reconstruction may also be created. The three dimensional reconstruction may be a formed model of the subject based upon the actual image data acquired of the subject. Thus, the model may be a generated, such as a computer generated, image for display with a display device. Two dimensional image data can include two dimensional x-rays that are acquired with selected imaging systems, such as fluoroscopy systems, C-arm imaging systems, and the like.

Additional data regarding the subject can be acquired including anatomical or physical measurements, prior procedures, and the like. The additional patient data may assist in planning a procedure, such as correcting for previous injuries and/or disease. Accordingly, it is understood that data acquired of a subject need not be limited to image data. The additional patient data may be used only to check or even select components, such as determining the size of a patient. Regardless of the data collected, following the receiving or the acquisition of data of a subject, the data may be generated for a viewing or evaluation of the subject data in block 26. The generation of the data can include the rendering of the three dimensional reconstruction based upon the two dimensional images. Further, the generation of the viewable data can include display of the three dimensional image data generated with appropriate imaging techniques, such as the MRI. According to various embodiments, however, the data of the subject can be displayed or generated for viewing or evaluation by a user. A user, such as a surgeon, can view the data for determining an appropriate plan. Further, the user may view the data and augment or confirm a plan generated based upon the image data acquired and the data of the subject acquired and evaluated by an appropriate system. The method 20 may be executed by a selected circuit or system, as discussed herein, as a stand-alone feature or it may be incorporated into various planning systems such as the Signature™ Personalized Patient Care System sold by Biomet, Inc. having a place of business in Warsaw, Indiana.

According to various embodiments, a user can provide input regarding various geometries and identified anatomical portions and a desired or proposed result(s) in block 30. The input in block 30 can be input into the method 20 such as through an input provided with a processing system. The input may be made via a touchscreen, keyboard, or mouse, etc. for inputting results or proposed results into a system to be achieved with the plan via the method 20.

Figure 2:
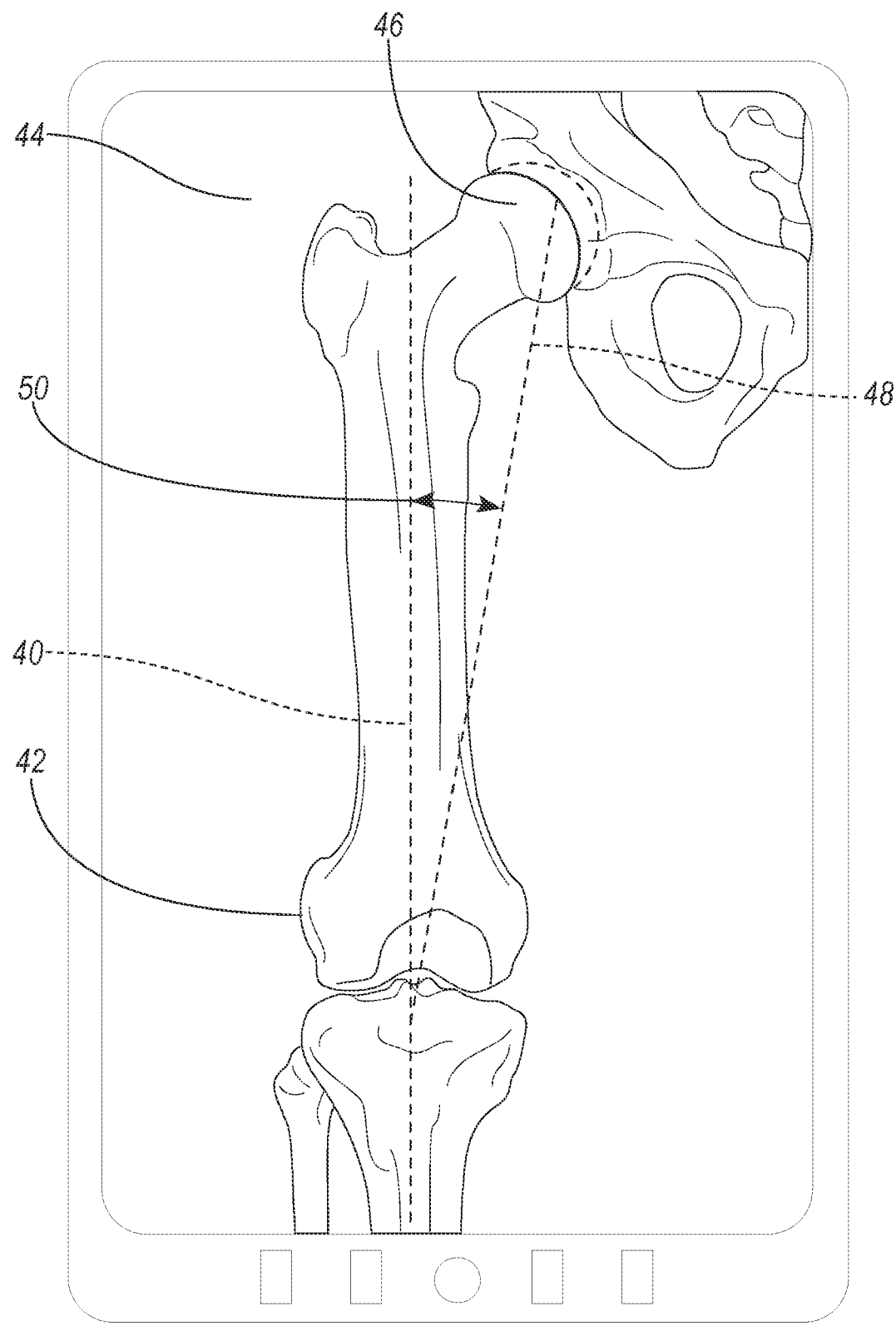
FIG. 2 is a display and system for providing input regarding an image data.

For example, with reference to FIG. 2, a user may identify an axis 40 of a femur 42, such as by drawing a line on a touchscreen display 44 with a finger or non-biological implement. A mechanical axis 48 extending from a femoral head 46 may also be determined. The mechanical axis 48 can be illustrated and an angle 50 between the mechanical axis 48 and the femoral axis 40 can be calculated or determined. The user, such as the surgeon, can identify or determine the angle 50 as a final angle that can be incorporated into a plan. The user may also augment or change the angle to the final desired or selected angle. The angle 50 may also be referred to as a valgus angle, which is an angle between the mechanical axis 48 and the femoral axis 40. It is further understood that analysis of the image data, such as viewed on the display 44, can be used to assist in determining an appropriate size for an acetabular prosthesis, a femoral head prosthesis, a femoral stem prosthesis, and other appropriate portions. It is understood that the selected sizes can be given a certain amount of variability or range such that more than one specific prosthesis component can be provided for a procedure. Thus, two or more sizes may be selected based upon viewing the image on the display 44.

The input from block 30 can allow the user to assist in determining various portions based upon the generated subject data from block 26. The input in block 30 may also allow the user to select results of a procedure. Results may include range of motion, valgus angle, etc. The selected results may be the results of the plan to be determined with the method 20, as discussed herein. The user, therefore, may provide to the system and/or method, medically and/or patient desired results of a procedure. It may also allow a user to provide desired results for a selected procedure, such as placement of a component in an complex mechanical system.

A determined plan in block 70, therefore, may be based, at least in part, on the input in block 30. The determined plan in block 70 can include identifying appropriate prosthetic components, sizes of appropriate prosthetic components, specific instrumentation for achieving a selected result, settings for selected instrumentation, and other appropriate outputs. Accordingly, various embodiments include outputting a plan in block 72, which may include outputting or identifying selected prostheses in block 74 and/or selecting and identifying instruments based on the plan in block 76. As discussed further herein, the output plan in block 72 can include identifying which prostheses, or a selected range of prostheses, is appropriate for achieving the determined plan in block 70. Further, the output plan in block 72 can include selecting instruments and/or selecting or identifying settings for the instruments in block 76.

For example, selecting prostheses or identifying prostheses in block 74 based upon the plan output in block 72 can include selecting a specific type of prostheses, such as a knee prosthesis that may include a Vanguard® Knee Prosthesis System or Oxford® Knee Prosthesis system both sold by Biomet, Inc. In selecting the prostheses, specifics may be determined and identified in the plan such as the size, a range of sizes, selected components (e.g., mobile bearing or non-mobile bearing) and other specifics relating to the selected prostheses for achieving the determined plan from block 70.

Figure 3:
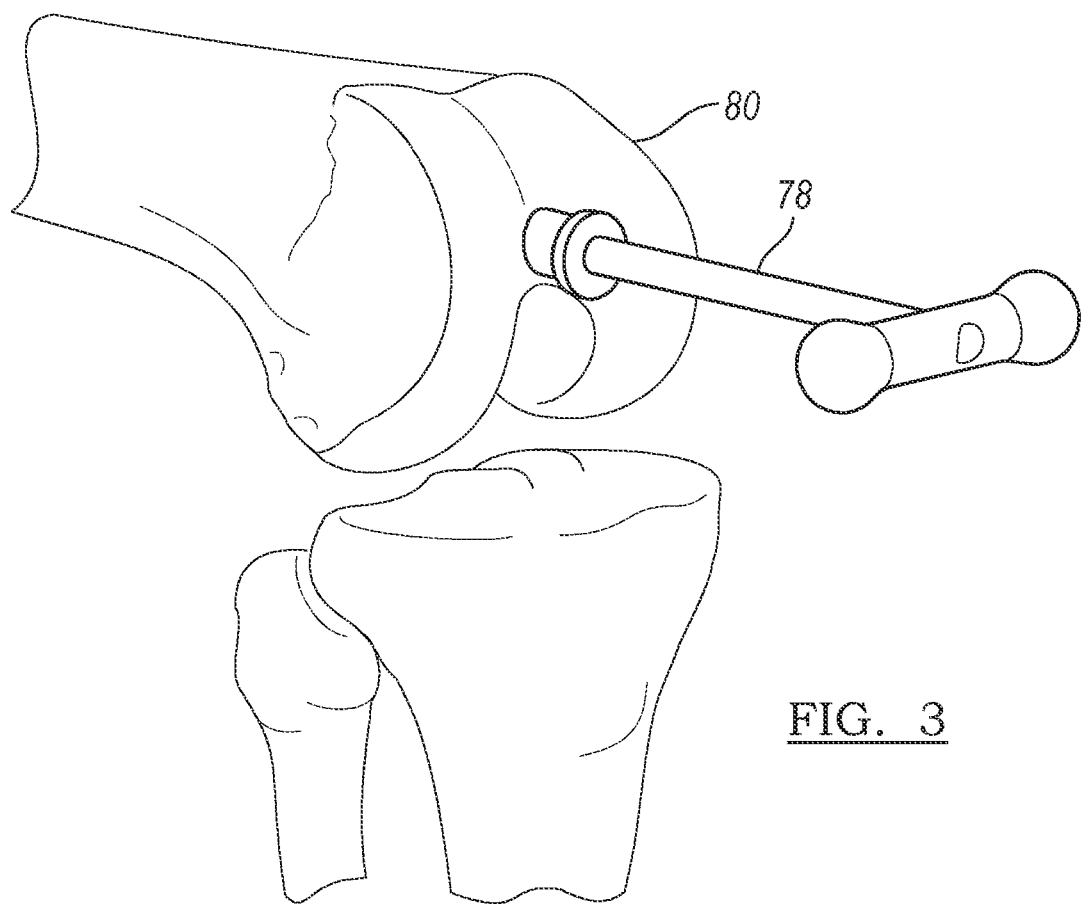
FIG. 3 illustrates accessing an intramedullary canal of a femur, according to various embodiments.

In various embodiments, the plan can include identifying a location for positioning an intramedullary (IM) rod 78, illustrated in FIG. 3, into a femur 80. The position of the IM rod 78 may be determined based upon known or predetermined instrument geometries, such as instruments provided with the Ascent® knee system sold by Biomet, Inc. The determination of the position for the IM rod 78 may be further based upon the determined and/or identified geometry of the anatomy by the user, as illustrated in FIG. 2. Further, the determined location of the IM rod 78 may be based on the selected or identified outcome from block 30.

Positioning the IM rod 78 into the femur 80 may be important and/or used in achieving the portions of the plan from block 72 as other instruments can be positioned relative to the IM rod 78 to achieve an appropriate resection and placement and/or a resection of the femur 80. Accordingly, in various embodiments, with reference to FIG. 3, the output plan in block 72 can identify a location for positioning the IM rod or inserting the IM rod 78 into the femur 80. The identified or determined location for the IM rod 78 may be delivered to a user, such as a surgeon with the delivered plan in block 110. In various examples, the plan may include a template (e.g. a transparent material that is visually aligned with predetermined portions of the femur 80) that is placed on the femur 80 with a visible target or point identifying where to place the IM rod 78. Alternatively, a three-dimensional (3D) model may be provided with the plan in block 110 identifying the location for the IM rod 78 in the distal femur, such as with a mark on the 3D model. Alternatively, a graphical display, such as with a display device, may include a picture of the distal femur based on the generated view from block 26 that illustrates the determined location for the IM rod 78. Still further, a guide, such as a patient specific guide, may be provided to guide drilling the IM rod 78 or forming a hole for the IM rod 78. It is further understood that all or any selected number of these may be provided together. The IM rod 78 may then be drilled, pushed, impacted or otherwise positioned within the femur 80 based on the plan output in block 72 that includes the determined location for the IM rod 78.

It is also understood, however, that the IM rod 78 may generally extend along the intramedullary canal of a bone, such as a femur 80. Thus, the output plan in block 72 may include or be based on the assumption that the user will place the IM rod 78 within the IM canal of the femur 80. The remaining portions of the output plan in block 72 may be based on this assumption.

It is understood that currently available instruments and prosthesis may be included in an accessible database that is used to achieve the plan in block 72. The known and/or stored geometries, sizes, etc. may be used to achieve the result input by the user in block 30. The system that is determining the plan in block 70 may access the database to determine those instruments, prosthesis, etc. to achieve the user input from block 30. Thus, based on the determined plan 72 and based upon the selected position of the IM rod 78 within the femur 80, selected instruments can be identified for positioning relative to the IM rod 78 to achieve results based upon the determined plan in block 70. In other words, instruments, such as a cut guide, may be placed on or connected to the IM rod 78 for performing a portion of a procedure. A cut guide may be connected to the IM rod 78 after the IM rod 78 is placed in the femur 80. Accordingly, placement of the IM rod 78 into the femur 80 may be based upon the plan output in block 72 to achieve the determined plan 70. The determined plan in block 70 is the plan that is determined to achieve the result (e.g. valgus angle) based upon the user input in block 30.

Figure 4:
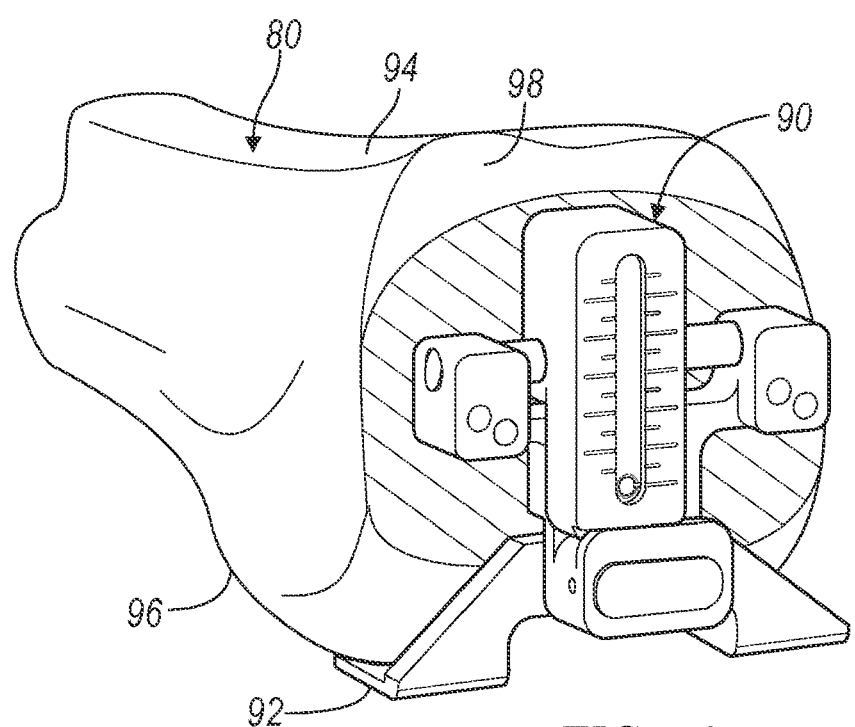
FIG. 4 illustrates sizing a femur, according to various embodiments.

Further, the output plan in block 72 can include selecting instruments based on the plan and/or selecting settings for instruments. For example, with reference to FIG. 4 an AP femoral sizer 90 may be positioned on the femur 80 relative to the IM rod 78, such as exemplarily being positioned over the IM rod 78. A cut block, such as a 4-in-1 cut block, e.g. the 4-in-1 AP chamfer guide sold by Biomet, Inc. with the Ascent™ total knee system, may also be connected with the IM rod 78 in a selected or determined position prior to the sizer 90. The AP sizer 90 may include one or more adjustable feet 92 that can be adjusted anteriorly and posteriorly relative to the femur 80. An anterior side 94 of the femur and a posterior side 96 of the femur 80 are considered when determining an amount of resection of the femur and/or selecting a prosthesis for positioning on the femur 80. Accordingly, the output plan 72 can identify specific and predetermined settings for the AP sizer 90 to achieve the preselected input results by the user in block 30. It is understood that other appropriate instruments may also be determined, such as a resection block for selecting an amount of a distal resection when positioned on the IM rod 78. Further, or alternatively thereto, Patient Specific or Custom Instruments may also be generated (e.g., by rapid prototyping) based upon the output plan 72. The Custom Instruments may also be positioned relative to the femur 80 based upon the IM rod 78 positioned within the femur 80. Custom implants or instruments, however, may also be formed to include a surface that will substantially mate with only a determined configuration of a specific patient, such as a bone and/or tissue surface.

The positioned IM rod 78, therefore, may be used to identify a reference point and/or reference location for various instrumentation used for performing a procedure. By having the IM rod 78 positioned within the femur 80 at the planned location, the instrumentation and/or prostheses can be positioned relative to the femur 80 to achieve the planned output in block 72. Thus, the input from block 30 that includes the selected result, such as a desired range of motion or valgus angle, may be achieved by performing the procedure based on the determined plan that is output in block 72.

It is understood that other selected instruments may also be provided that allow for selectability. For example, a patient-specific distal femoral sizer may be generated and manufactured based upon the plan determined in block 70. The patient-specific sizer may also be positioned on the IM rod 78, once the IM rod 78 is within the femur 80. The patient-specific sizer may be based upon the plan determined in block 70 and may include appropriate orientation and/or contact points to engage the distal femur 98 prior to any resection. Nevertheless, both a multiple use adjustable system and/or a single-use substantially patient-specific system may be used as the selected instruments based on the plan 76.

Further, the selected prostheses from block 74 may be based upon the plan 70 which is based upon the user input from block 30. The selected prostheses in block 74 can include a size, size range, and type of prosthetic components. For example, for a total knee arthroplasty, a prosthetic system may include a tibial plateau prosthesis, a tibial bearing prosthesis, and a distal femoral prosthesis. Each of these prosthesis components may be provided in several sizes. To achieve an appropriate size for a selected range of patient population (e.g., 99%) several components of various sizes may be required, such as six distinct sizes of each of the three components. Based upon the plan from block 70, however, it can be determined that the specific patient is within a range of one or two sizes of each of the components. Thus, only the selected component sizes may be delivered for a selected procedure. This allows for the procedure to occur with a minimal amount of components for selection by a user and a minimal preparation and related or associated costs for cleaning, manufacturing, or the like of the components.

Figure 5:
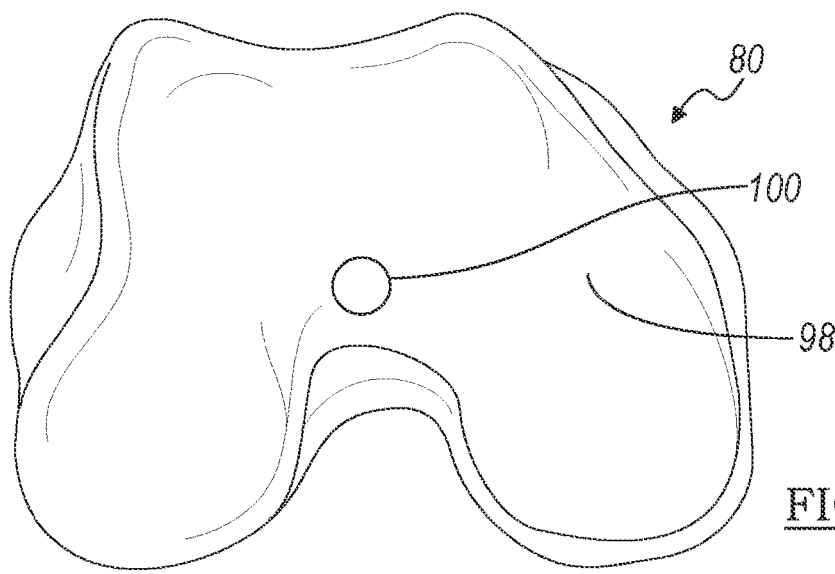
FIG. 5 illustrates a distal femur, according to various embodiments.
Figure 6:
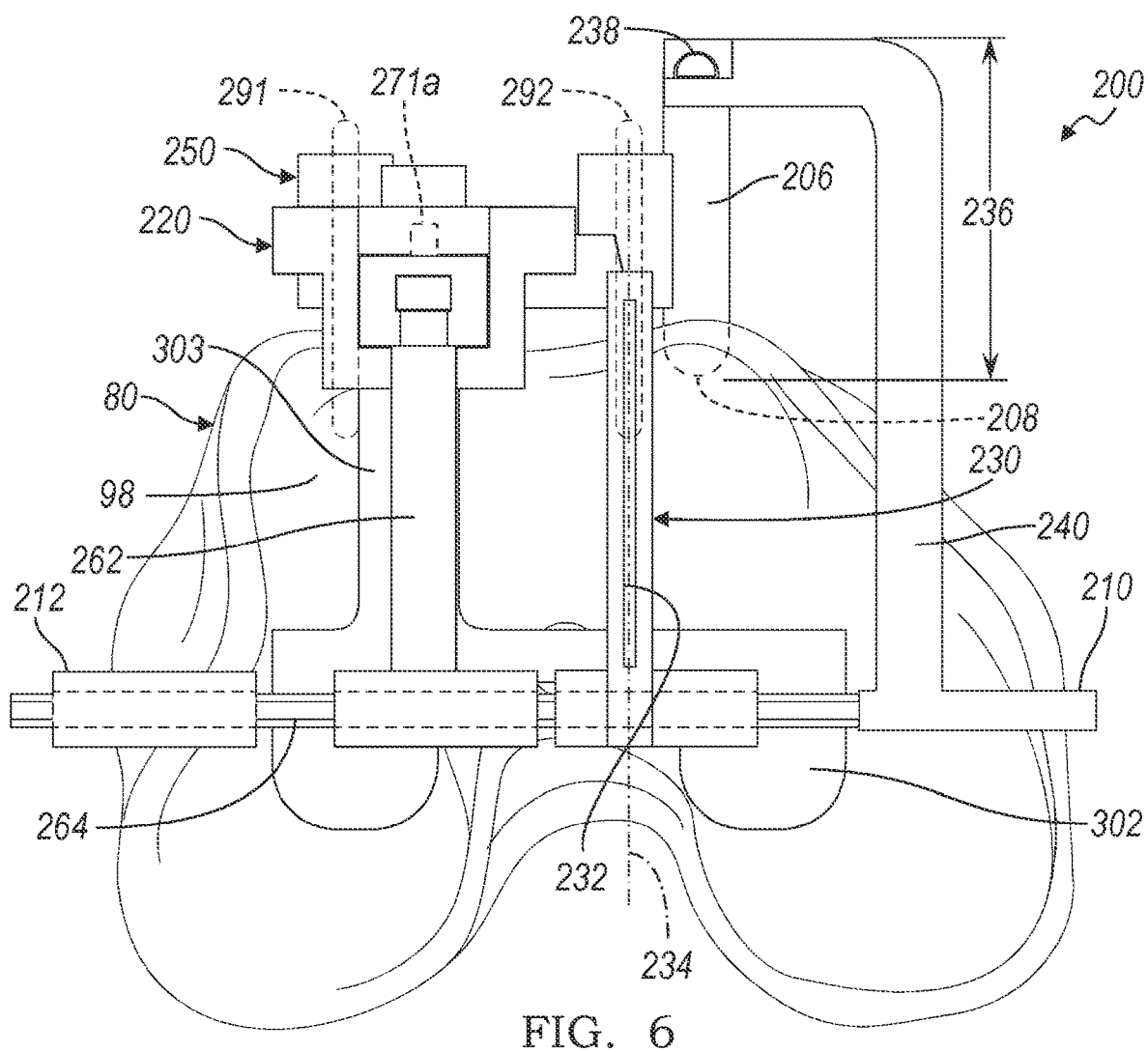
FIG. 6 is a front environmental view of an alignment system for a femur, according to various embodiments.

The output plan in block 72 can also include written or electronically transmitted instructions to a user. The output of the plan in block 72 can identify to the user the selected range of sizes for the components, settings for an adjustable instrument system, and a proposed placement for the IM rod 78. With reference to FIG. 5, for example, the output of the plan 72 may include a visual illustration of a distal portion 98 of the femur 80, as discussed above, with a target or access location 100 indicated thereon. The illustration of the access point 100 may be a target or selected point for insertion of the IM rod 78 into the femur 80. The illustration of the distal femur 98 can be based upon the image data generated or accessed by the method 20. The plan output in block 72 may also include a 3D model, 3D image, written instructions, etc.

Thus, a user may be able to identify the target location 100 from the output, illustrated in FIG. 5, on the specific patient. The target location 100 is determined as part of the plan determined in block 70 to achieve the desired or selected result that is input in block 30. The IM rod 78 may then be inserted into the patient to ensure that the plan is carried out based upon the generated image data and the identified plan.

Further, the output in block 72 may include the determined specific settings, such as locations of the portions of a reusable sizer, for determining an appropriate progression of the plan. Further, the output of the plan 72 may include identification of a portion of a cut block to be used to ensure an appropriate resection of the distal portion of the femur 80 and other portions of the plan. Thus, the output of the plan for block 72 can allow a user to achieve the results input by the user in block 30 based upon the determined plan block 70.

After the plan has been output in block 72, the prostheses selected in block 74, and the instruments that have been selected in block 76, and any other selection portions, can be delivered. For example, the plan can be delivered in block 110, the selected prostheses can be delivered in block 112, and the instruments can be delivered in block 114. It is understood, according to various embodiments, that the selected instruments can also be manufactured in block 116. As discussed above, the instruments can be based upon the plan output or determined in block 70 for a specific patient (i.e. single patient). Accordingly, the instruments may be manufactured based upon the plan determined in block 70. These instruments may be manufactured in block 116 after the selection of the instruments in block 76. It is understood, however, that the instruments may not be or need not be patient specific. The output plan in block 72 can include specific settings (e.g. sizes) of generalized instruments that are adjustable for selected procedures. It is further understood, according to various embodiments, that selected prosthesis may also include patient specific or designed prosthesis that are manufactured or designed in block 118. If the database of prostheses does not include a prosthesis to achieve the input results in block 30 then a patient specific one may be determined. The patient specific prosthesis may be designed and manufactured in block 118 and then delivered in block 112.

Each of the portions can be delivered according to various commonly known techniques, such as electronic transmission, postal delivery, courier delivery, or other appropriate delivery systems. For example, the plan can be delivered on block 110 via an electronic transmission from a plan provider, such as Biomet, Inc. via known delivery systems including those incorporated with the Signature™ Patient-Specific System or other appropriate delivery systems. The prostheses and instruments can also be delivered in blocks 112, 114 according to appropriate and generally known techniques. The method 20 can then end in block 120.

Ending the method in block 120, however, is understood to possibly precede performing a procedure on a patient based upon the determined plan in block 70. That is, after the plan, prostheses, and instruments are delivered in blocks 110-114 the user may perform a procedure on a selected subject, such as a human patient, with the delivered items. In performing a procedure, the delivered plan from block 110 may be followed and the user can use the delivered instruments from block 114 to implant the delivered prostheses from block 112. As noted above, the delivered instruments from block 114 can be used to achieve the plan output in block 72, which has been determined in block 70. The delivered prostheses in block 112 may allow for the user to select an appropriate prosthetic member from a limited range of sizes, rather than all possible sizes, based upon the determined plan in block 70. Thus, the user can perform a procedure based upon the determined plan 70 to achieve the selected results in block 30.

Generally, therefore, the method illustrated in FIG. 1 may determine a plan to achieve a desired or selected result chosen and input in block 30 by the user. The user may be a surgeon. Based on the input from block 30 along with the generated data/view in block 26, the system may determine the plan in block 70. In determining the plan the system may access the database of known and/or available instruments along with known and/or available prostheses. Each of these known and/or available instruments along with known and/or available prostheses may be analyzed using their known geometries and sizes to determine the plan in block 70 that would achieve or best achieve the input result from block 30. For example, the input desired result may be a selected range of motion (ROM) and valgus angle. The system may then analyze the generated subject data and the database of instruments and prostheses. The system may then determine which instruments, which specific settings for the instruments, and which specific prosthesis(es) may achieve the input result. The system may then determine the plan in block 70 and output the plan in block 72 including the identified and selected instruments, settings, and prostheses. Also, the system may determine designs for instruments and prostheses, if the database does not include appropriate instruments and/or prostheses. All of this may occur prior to the beginning of a procedure, such as before placing a subject in an operating room. Thus, instrument and prosthesis selection may precede initiating a surgical procedure. Further, the user, such as a surgeon, may only be required to input a selected result and the system determines the plan to achieve the result.

In addition to the illustrated method 20, various instruments and devices may be used to assist in a procedure. For example, various guides and templating instruments can be positioned relative to a portion of anatomy, such as the distal femur 98, for performing a procedure. According to various embodiments, the instruments can be positioned relative to the distal femur and adjusted according to a predetermined plan. For example, the method 20 can be used to assist in identifying or positioning a template or instrument relative to a distal femur based upon settings provided to a user, similar to those discussed above.

According to various embodiments, the distal portion 98 of the femur 80 may be prepared or oriented based upon a predetermined plan, such as the plan illustrated in FIG. 1, using an alignment guide 200 illustrated in FIGS. 6, 7, 8, and 9. The guide 200 can be oriented relative to femur 80 as discussed further herein, including the distal portion 98. Generally, the guide 200 can be adjusted relative to the femur 80 for orienting various portions to be positioned relative to the femur and/or to sections of the femur. For example, a rod or drill holes can be formed into the femur for performing various resections of the femur including a distal, proximal, posterior resections, and the like.

According to various embodiments, the guide 200 may include an anterior stylus or contact member 206 that can include a contact point 208 to contact an anterior portion of the femur 80. The contact point 208 can contact the femur 80 at a predetermined position of the alignment guide 200 relative to the femur 80 based upon various embodiments. The anterior contact point 208 may contact the femur 80 based upon the predetermined plan, such as based upon image data of a subject including the femur 80. The image data can include a three-dimensional rendering based upon three-dimensional image data such as a MRI, computed tomography image, or other appropriate images. Further, the three-dimensional reconstruction can be based upon a selected number of images, such as one or more images such as an anterior-to-posterior x-ray two-dimensional image or a medial-to-lateral two-dimensional x-ray image.

The guide 200 may include a lateral contact member 210 and a medial contact member 212 and they point to and/or contact the insertion 'point' or location of collateral ligaments. The horizontal bar seen in FIGS. 6 and 7 align on the femur 80 at an appropriate epicondylar axis as is generally understood by one skilled in the art. The epicondylar axis may include a line that extends medial to lateral on the femur 80 that interconnects a medial epicondyle and a lateral epicondyle in a substantially straight line across the femur 80.

According to a selected plan, such as the plan output in block 72, the guide 200 can be adjusted according to various considerations, including the femur 80 of a specific patient. Certain portions, such as a stylus 206, may be designed and formed for a single specific patient, as discussed herein. The contact points 210, 212 may be movable relative to the guide 200 such that they may be moved to contact medial and lateral points on the femur 80. Once contacting the medial and lateral points (such as the medial and lateral epicondyles), the anterior contacting point 208 may contact an anterior point on the femur 80. To further assist with a patient specific alignment, the guide 200 may include a patellar groove alignment or viewing portion 230. The patellar groove alignment portion 230 may include a window 232 that can be aligned with the patellar groove 234. The patellar groove 234 may be generally positioned between a medial and lateral condyle to the femur 80.

The stylus 206 may be designed and formed to include substantially patient specific features and/or portions. For example, a length of the stylus may be specific to a single selected patient, based on the obtained data and the user input. Further, the contact point of the stylus 206 may be formed to complement or mate with a selected or identified portion of the femur 80. Also, a geometry, such as a curve (medial-lateral, anterior-posterior, or combinations thereof) may also be specific to a single patient such that the contact portion of the stylus will mate with substantially single portion of the femur of the patient. For example, the contact may include a mirror or inverse contour of the selected contact portion of the patient.

Once the selected contact points have been contacted with the guide 200, the specific plan may be achieved by adjusting an adjustment system 220. The adjustment system 220 may include a dial or moveable portion 221 that allows a user to move the guide member 250 relative to a distal surface 98 of the femur 80. By aligning the opening 232 of the patellar groove alignment portion 230 along with the medial and lateral epicondyle contacts 210, 212 the guide 200 can be aligned relative to the femur anteriorly and posteriorly, and medial laterally. The adjustment system 220 may allow adjustment of the guide 200, such as moving the guide block 250, to contact the distal femur surface 98 in a specific configuration and position. Thus, the guide 200 may be adjusted to be positioned relative to the femur 80 in a substantially patient-specific manner. In other words, the settings may be based on the plan for the specific patient and the guide 200 may be so adjusted. Additionally, adjustment system 220 need not have numbers and adjustments may be based on what is found during surgery to touch existing geometry of the femur 80. For example, especially for CT and X-ray data, the cartilage is not seen.

The alignment guide 200, with continuing reference to FIGS. 6-9, can include various portions to contact the distal portion 98 of the femur 80. According to various embodiments, the stylus 206 can be a substantially patient-specific portion that includes patient-specific dimensions. For example, an inferior-to-superior dimension 231 may be selected for a specific patient. The inferior-to-superior dimension 231 can be a dimension where the stylus 206 interconnects with the guide 200 at a first point 233 and contacts the patient or the femur 80 at the contact point 208. Thus, the dimension 231 can allow for ensuring that the guide 200 contacts the femur 80 at a selected position while accounting for the inferior-to-superior dimension 231 based upon a contact point of the stylus 206 relative to the femur 80. Further, the stylus 206 can include an anterior to posterior dimension 236 that extends from the femur contact point 208 to a top region 238 of the stylus 206. The anterior to posterior dimension 236 can allow for ensuring that the guide 200 is at a selected anterior position relative to the femur 80. The stylus 206 allows the guide to be positioned anterior-posteriorly and the contact points 210, 212 help ensure medial-lateral alignment. These alignments and contacts can be based on the selected position of the guide 200 relative to the femur 80, such as selected during a patient and procedure planning step in the method 20.

Again, the guide 200 can include medial and lateral contact points 210, 212 on a substantially rigid guide portion that extends substantially along a line of the guide 200 that may be positioned medial to laterally on the femur. A stylus holding arm or member 240 may extend from the alignment guide portion substantially in a superior dimension or direction when the guide 200 engages or is contacted to the femur 80. The stylus 206 may be engaged with the holding arm 240 to position the stylus 206 relative to the femur in a predetermined and substantially patient-specific configuration. Accordingly, the guide 200 may include substantially reusable non-patient specific portions, such as the alignment portion interconnecting the medial and lateral contact or alignment members 210, 212, that are used in conjunction with patient-specific portion(s) such as the stylus 206. As discussed above, however, the stylus 206 may be formed for a specific patient to contact a selected configuration or portion of the patient, including an anterior portion of the femur 80. For example, the dimensions 231 and 236 may be specific to a single selected patient. Also, settings as discussed herein, may be provided that are patient specific. Additionally, the stylus 206 can be adjustable and then set in the surgery based upon data determined from the plan.

Figure 10:
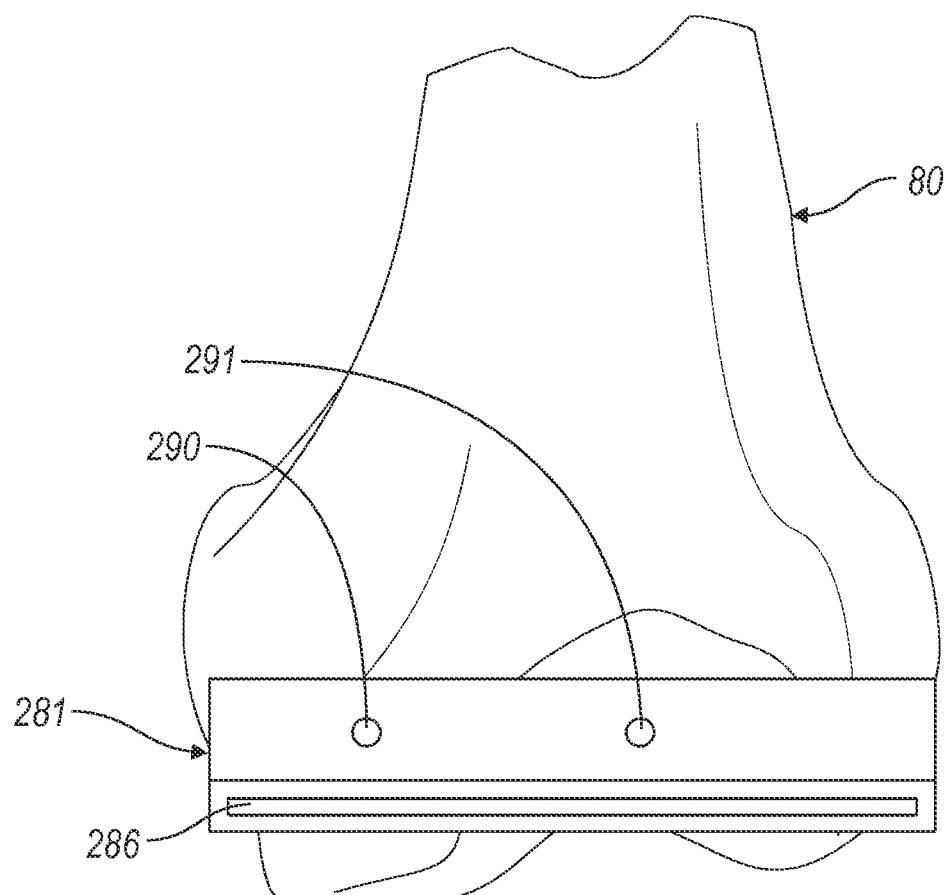
FIG. 10 is an environmental view of a distal cut block positioned next to a femur.

Once the stylus contact 208 has contacted the anterior portion of the femur 80 and the guide 200 is aligned relative to the contact points 210, 212, a pin placement member or alignment block 250 may be moved relative to the stylus 206 via the adjustment mechanism 220. The pin placement member 250 may include a first pin placement passage 252 and a second pin placement passage 254. It is understood that a single pin placement passage or more than two-pin placement passages may be provided in the pin guide member 250. The passages 252, 254 may be provided to guide a placement of one or more pins (291, 284, FIG. 10) into the femur 80. According to various embodiments, the pin may allow for engagement of a cut block, such as a distal cut block (281, FIG. 10), for a femur including the distal cut block for use with the Ascent™ knee system, sold by Biomet, Inc. for performing a distal cut on the femur 80. The pins are set into the femur through the passages 252, 254. The pins help define an amount and position of the cut performed by the distal cut guide by engaging the set pins with the cut block prior to performing the distal resection, as illustrated in FIG. 10 and discussed herein.

Figure 7:
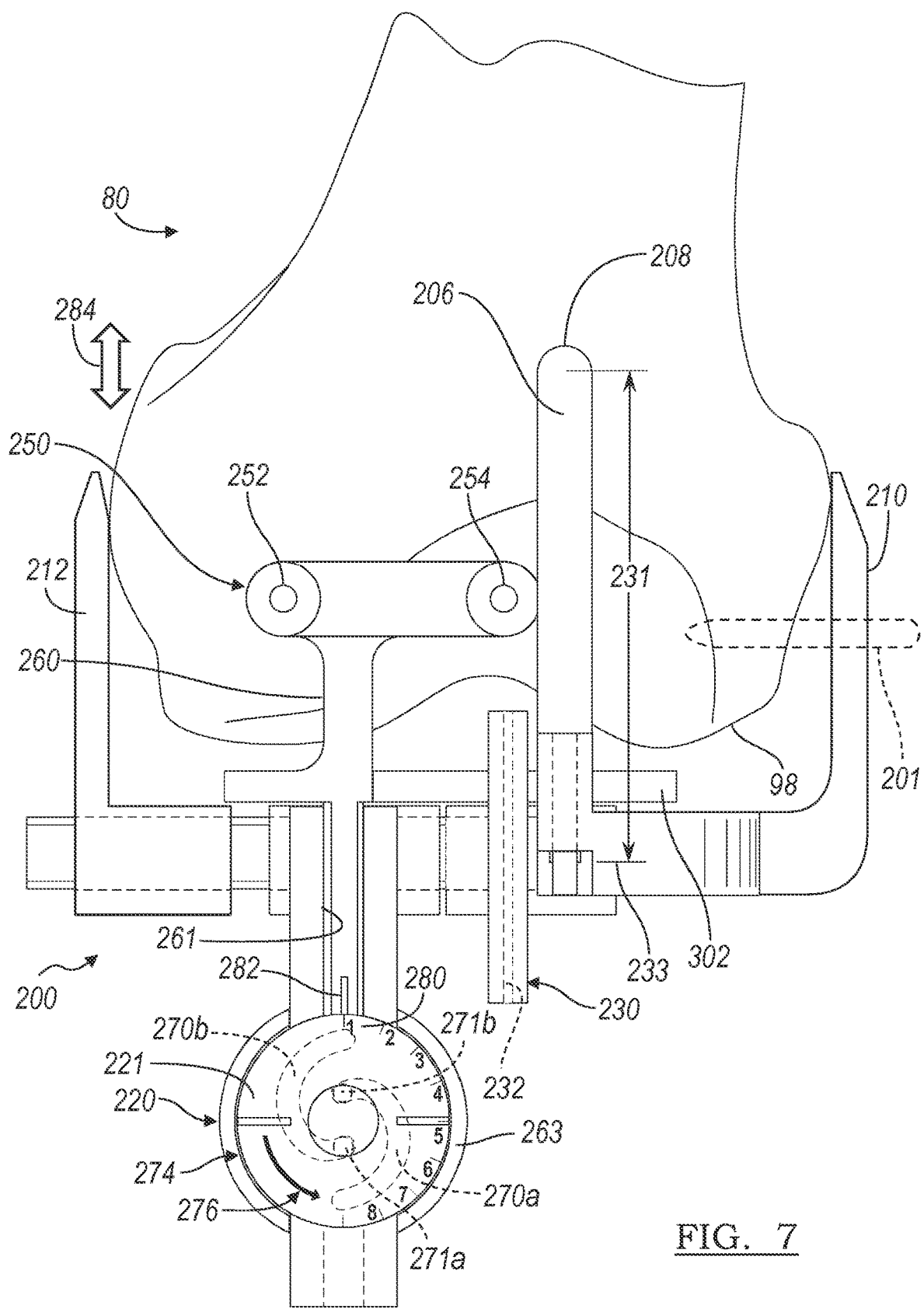
FIG. 7 is a top environmental view of the alignment system of FIG. 6.

Alternatively, the cut guide 281 could replace the pin guide 250 directly. The cut guide 281 may be held in place by an attachment mechanism (not illustrated but may include magnets, threaded pins or screws, clips, etc.) which may potentially reduce steps. Further, separate pins 201 or other attachment mechanisms, as illustrated in FIG. 7, may be used or placed to stabilize the guide 200 on the femur 80. If the pins 201 are used before adjustment of the foot 302 adjustment, the pins 201 must be placed to not restrict motion of the foot 302 and the pin placement block or guide 250.

Figure 8:
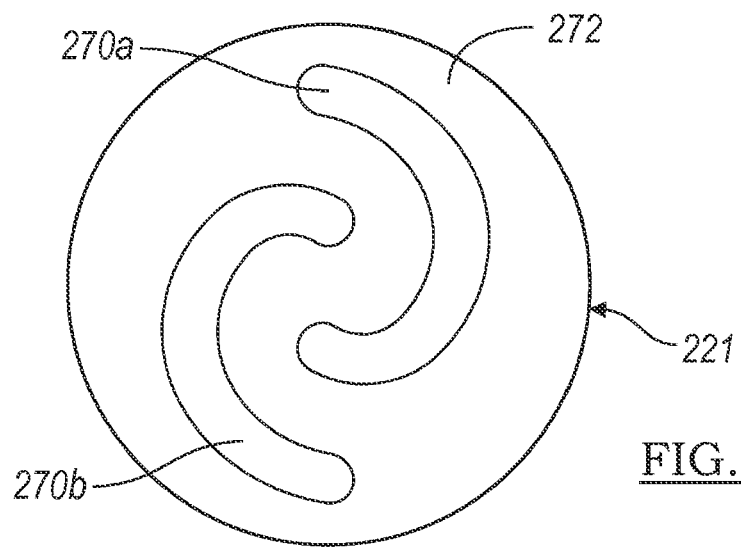
FIG. 8 is a detailed view of a second surface of a portion of the alignment system of FIG. 6.

The pin placement block 250 can be moved relative to the stylus 206 via the moveable member 221 and a movement or holding member 260 that is moved by the moveable member 221. The movement member 221 can be provided as any appropriate member in combination with the holding member 260. For example, a screw gear or worm gear mechanism can be provided to move the guide block 250 relative to the stylus 206. According to various embodiments, however, a nautilus groove 270, as illustrated in FIG. 8 can be provided in a surface 272 of the moveable member 221. The nautilus groove 270 can engage at least one pin 271a that extends from the holding member 260 into the nautilus groove 270. The member 221 may include a double nautilus groove 270, which includes a first groove portion 270a and a second groove portion 270b. In the illustrated example, the second groove portion 270b may engage a second pin 271b. The nautilus groove 270 may include the groove 270 that is formed in the member 221 that includes an increasing distance from a center of the member 221 over the length of the groove 270 or respective groove portions 270a, 270b. Thus, as the first member 221 is moved, for example, in a clockwise direction as indicated by arrow 276, the holding member 260 can move in a first direction which moves the alignment member 250. Rotating the first member 221 in an opposite direction, such as a counter-clockwise direction can move the holding member 260 in an opposite direction. Therefore the double nautilus groove 270 makes the pins 271a, 271b move relative to each other and the first member 221. In the design they move equally in opposite directions.

The first member 221 may include markings, such as numerical markings 280 that may be moved relative to an indicia 282 formed on the guide or holding member 260. By aligning the markings 280 with the indicia 282, a selected position of the guide member 250 can be made relative to the stylus 206. Generally, the guide member 250 can be moved generally in the direction of arrow 284 by rotating the first member 221 in a clockwise or counter-clockwise direction. Thus, the alignment block or member 250 can be moved relative to the stylus 206 to position the alignment block 250 and the passages 252, 254 for positioning the guide or holding pins relative to the stylus 206. In addition, other mechanisms may be used to move the adjustment system or mechanism 220. For example, motors may be driven based on instructions received from a transmitter. The instructions may be first processed with a processor provided with the guide 200 to move the motors and, thus, the adjustment. Also a key member may be formed that will move the adjustment member to a selected position. All of the adjustments may be based on the plan, as discussed above.

In various embodiments, numerical markings 280 may not be necessary or provided. For example, in various imaging techniques, such as CT imaging and X-ray imaging data, the cartilage is not seen or relatively indistinguishable and adjustments would be based on what is found during surgery to touch existing geometry, such as bone geometry. Thus, the guide 200 may be aligned using the boney landmarks available during the generation of the plan, as discussed above. For example, once the guide is aligned with the epicondyles, a line that connects the epicondyles, and or the patellar groove, and the stylus has engaged the anterior portion of the femur 80, the guide is known to be properly positioned based on or according to the plan. As discussed above, various portions that are viewable in images, such as a line that connects the epicondyles, and or the patellar groove, may be used to ensure that the guide or any instrument portion is aligned according to the plan based on the images. Thus, the procedure may proceed according to the plan. A numerical setting would not be necessary, the foot 302 may be efficiently moved towards the femur 80 and once the foot 302 contacts the femur 80, when the remaining portion of the guide 200 is positioned according to the plan relative to the femur 80, the pins 291, 292 may be placed in the femur 80 through the block 250.

As discussed above, the specific marking of the group of markings 280 to be aligned with the alignment indicia 282 can be determined based upon the patient-specific plan determined in a method 20. The selected marking can be transmitted to a user, such as a surgeon, for use during a selected procedure. Accordingly, based upon a specific patient, the moveable member 221 can be selected to be positioned at marking "4" to select a position of the alignment block 250 relative to the stylus 206. This can be transmitted to the user and the user can adjust the adjustment system 220 to the selected marking relative to the alignment indicia 282 during the procedure. Based upon and after moving the adjustment system 220, the alignment block 250 can be positioned relative to the femur 80 based upon the patient-specific plan and the alignment block 250 can be used to guide pins through the passages 252, 254. It is also understood, that the passages may be used only to form pilot holes into the femur. The guide 200 may then be removed and the pins placed in the pilot holes. The movement member 260 may move in a track or groove 261 formed by a support member 262. The support member 262 may moveable hold the moveable member 221 within a wall or portion 263 and allows the moveable member 221 to apply a force to the movement member 260 when it is turned, as discussed above, vis the nautilus grooves 270a, 270b and the pines 271a, 271b. The support member 262 extends from a cross or support member 264. The contacts points 210 and 212 may be formed by members that are at terminal ends of the support bar 264. Further, the groove alignment portion 230 and the stylus holding arm 240 may also extend from the cross support arm 264.

The guide 200 may also include a distal femoral contact member or foot 302. The foot 302 may extends towards the posterior of the femur 80. The distal contact foot 302 can contact a portion of the condyles near 98 of the femur 80. The alignment block member 250 may move with or separate from the distal contact foot 302. According to various embodiments, contact or alignment with the stylus 206 and at least one of the medial or lateral contacts 210, 212 provide appropriate alignment with the femur 80. The distal contact foot 302 may extend from the block 250 via an extending arm 303 and may move with the block 250 to assist in stabilizing and or positioning the block 250 relative to the femur 80. Once positioned and stabilized, the block 250 may then be used to make passages into the femur 80 through the guide holes 252, 254. Thus, when the selected subject landmarks are identified in the procedure on the subject, such as on the femur 80, the contacts points 208, 210, and 212 may be aligned or positioned to contact the landmarks. Thus, the guide 200 is properly positioned for the specific subject to allow the block 250 to align the holes 252 and 254 once the foot 302 contacts the distal femur 98, the block 250 is otherwise stopped relative to the femur 80, and/or the proper and preselected number is aligned with the marking 282.

With reference to FIG. 10, once the passages 252, 254 have been used to position pilot holes and/or pins (e.g. 290, 291), a distal femoral cutting block 281 can be connected to the pins, such as a first pin 290 and a second pin 291, via passages or bores formed in the cut guide 281. The distal cut guide 281 is then positioned at the distal end of the femur 80 according to a predetermined plan, as discussed above. A cut guide slot or portion 286 is positioned to allow for resecting the distal portion of the femur 80. As is understood by one skilled in the art, a saw may pass through the cutting slot 286 to resect the distal end of the femur 80. Once the distal resection is performed, according to any appropriate method, the distal cut block 281 can be removed from the femur 80. The alignment pins 290, 291 can be maintained within the femur 80 for further alignment purposes or can be removed from the femur 80 once the distal resection is performed.

In summary, the alignment guide 200 can be used, at least according to the method discussed above, to position the alignment pins 290, 291 in the femur 80 at locations according to the predetermined plan. The pins can help position and stabilize the distal femoral resection guide 281 to perform a distal resection of the femur 80. The plan for positioning the pins 290, 291 in the femur 80 with the guide 250 can be planned with a planning system including the Signature® Planning System sold by Biomet, Inc. and/or using the method 20 discussed above. As discussed above, the positioning of the pins 290, 291 for the distal cut guide 281 can be geometrically determined and modeled in the software and based upon image data of the subject at a selected position for the distal cut guide 281. Based upon this, the positioning of the pins can be determined for achieving the selected cut with the guide 281 to achieve a selected shape of the femur 80 for positioning a prosthesis on the femur 80.

Figure 9:
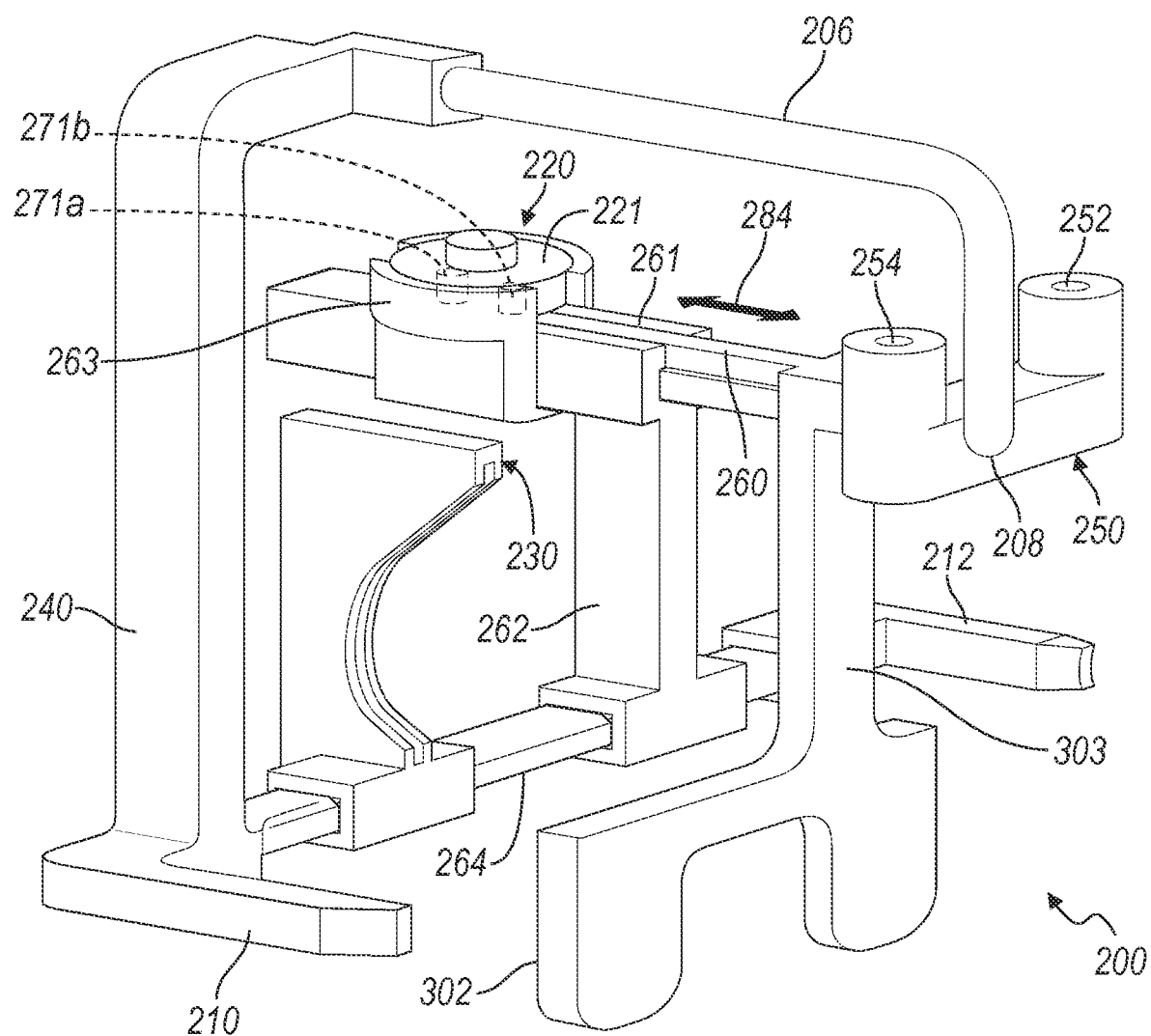
FIG. 9 is a second perspective view of the alignment system of FIG. 6.
Figure 9A:
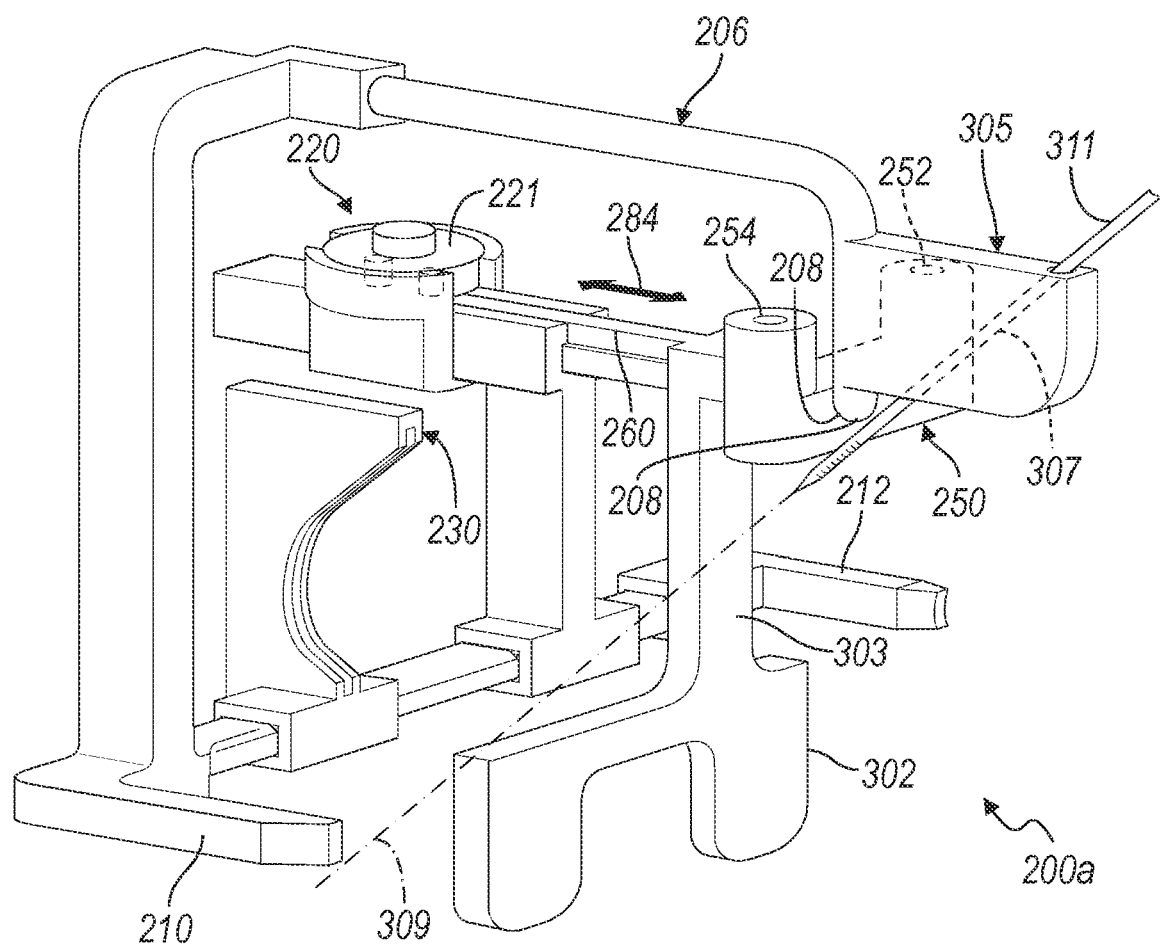
FIG. 9A is a perspective view of an alignment system according to various embodiments of FIG. 6.

With reference to FIG. 9A a guide 200a is illustrated. The guide 200a can be substantially identical to the guide 200, discussed above, save for those portions noted below. Generally, the guide 200a can include various portions that are configured or designed to point to or contact various portions of the anatomy such as the epicondyle contact or members 210, 212, the stylus 206, and the foot 302. In addition, however, various portions can be used to substantially fix, at least in one dimension, the guide 200a relative to an anatomy, such as the femur 80.

According to various embodiments, a drill guide 305 can be integrated with the stylus 206 as a single member or may be interconnected with the stylus 206 according to various mechanisms, such as a locking taper fit, a threaded connection, or other appropriate connection mechanism. Regardless, the drill guide 305 can include a guide bore 307 that extends through the drill guide 305. The guide bore may extend along an axis that is substantially parallel or aligned with an axis or line 309 that extends between the lateral contact member 210 and the stylus contact point 208. A drill bit or drill pin 311 may be drilled through the guide bore 307 and into a bone, such as an anterior portion of the femur 80.

The drill pin 311 can then be maintained within the drill guide 305 such that the drill guide 305 is only able to rotate about an axis defined by the drill pin 311 that is positioned within the guide bore 307. This can allow the guide 200a to also rotate around the guide pin 311, but be at least partially stabilized relative to the femur 80 by the guide pin 311 that is drilled into a subject portion, such as the femur 80. Accordingly, the drill pin 311 can be fixed into a portion of the subject, such as the femur 80, and the other bone contacting or pointing portions, such as the lateral and medial upper epicondyle contact or pointing portions 210, 212 and the stylus contact portion 208, can be positioned to contact the femur to ensure that the guide 200 is positioned and stabilized relative to the femur 80 according to the plan.

It is understood that the drill pin 311 can be positioned within the anatomy, such as the femur 80 or any other portion of the subject, when the various portions of a guide 200a are aligned with portions of the femur 80, as discussed above. Accordingly, the guide can be initially positioned and the drill pin 311 can be drilled into the anatomy and then the guide 200 is finally positioned and the foot 302 can be positioned against the femur 80. The drill pin 311 can then stabilize the guide 200a along with the other bone contacting portions, such as the stylus contact 208 and the foot 302 when the pins 291 and 292 are positioned through the guide bores 252, 254. It is understood that the axis of the drill pin 311 can generally be positioned near or on the line 309, but need not be positioned directly on the line 309 to appropriately and selectively stabilize the guide 200a relative to the portion which the drill pin 311 is positioned, such as the femur 80.

Once the distal cut has been completed, the procedure may follow selected procedure steps, such as positioning an intramedullary rod, if selected, and sizing the distal femur for positioning a further cut block. It is understood that certain steps, such as positioning the IM rod 78 may not be selected or necessary. Additional cut blocks may include the 4-in-1 cut block to make various other cuts of the femur 80, including a posterior and anterior cut and respective chamfer cuts. The method, therefore, may continue by positioning the sizer 90 relative to the cut portion, as similarly illustrated in FIG. 4. Accordingly, the alignment guide 200, 200a can be used to align positioning of the distal femur cut block pins 291, 292 and determining the position on the femur 80 of the position for an IM rod for other portions of the procedure.

In addition to or alternative to use of the sizer 90, as discussed above, an adjustable cut block may be used. The adjustable cut block may include an adjustable 4-in-1 cut block 400, with reference to FIGS. 11 and 12. The adjustable cut block 400 can be used as an alternative to the sizer 90, as discussed further herein.

The adjustable cutting block 400 may include various portions that can adjust to one another. Generally, the adjustable cut block 400 may include an anterior guide portion 410, a posterior guide portion 420, and a chamfer guide portion 430. The anterior guide portion 410 may include a guide slot or edge 432 that can be used to guide a saw blade. For example, the guide portion 432 can be a slot into which a saw blade is positioned to guide the saw blade to make a selected anterior cut. Similarly, the posterior guide portion 420 may include a guide slot 434 that may also receive a blade to perform a posterior resection. The chamfer guide portion 430 may include edges or surfaces, such as an anterior chamfer guide surface 436 and a posterior chamfer guide surface 438 rather than receiving within a slot, the saw blade may be positioned against the respective surfaces 436, 438 to make the respective anterior and posterior chamfer cuts. Thus, the blade is not captured but is held against the respective surfaces 436, 438 by a user or other mechanism to make the respective cuts. Nevertheless, it is understood by one skilled in the art that a slot may also be formed that includes the surfaces 436, 438 for making chamfer cuts. Using a 4-in-1 cut block having slots and/or guide surfaces is generally known to one skilled in the art and may be similar to the 4-in-1 cut block used with the Ascent™ knee system sold by Biomet, Inc.

The adjustable cutting block 400 can include various bone holding portions, such as a first projection 450 having an aperture 452 through which a fixation pin may be placed. A fixation pin, illustrated in phantom 454, may extend through the projection 450 via the aperture 452 to be fixed into the femur 80. A second projection 460 may include a second aperture 462 and a pin (shown in phantom 464) to engage the femur 80. The pins 454, 464 may also be placed in other locations to fix the cutting block to the femur 80, such as though portions (e.g. ends) of the chamfer block 430. Additionally, if the sizer 90 (FIG. 4) is used, the sizer 90 may allow for drilling holes to position the block 400. If that is done, pegs 454, 464 may be included on the posterior block 420, this may also preclude the need for a foot 470.

The fixation of the adjustable cutting block 400 may occur after selecting an appropriate size of the more than one 4-in-1 cutting block to determine and/or make appropriate anterior and posterior cuts of the femur 80. For example, the engageable member or foot 470 (also referred to as a posterior foot) can engage the cut slot 434 on a posterior edge of the cutting guide 400. A posterior contacting foot or ledge 472 may contact a posterior portion of the femur 80 to position the cut guide 400 at a selected position relative to the femur. The posterior foot 470 may include a selected offset or rotation angle 474 relative to an axis 476 of the cut slot 434. A line 478 can extend along the bottom edge of the foot 470 to define the angle 474 relative to the axis 476 of the cut slot 434. The appropriate angle can be any selected angle and can be determined during a planning step based upon image data of a subject. Further, the posterior foot 470 can be removably positioned within the slot 434 for selective engagement with the cutting guide 400 to allow for adjustment of the cutting guide 400. Additionally the foot 470 may have an adjustable angle.

An anterior stylus 480 may include an anterior contacting point 482 to contact an anterior portion of the femur 80. The stylus 480 can be removably connected, permanently connected, or formed as one piece with the guide 400. The stylus 480 can contact or be interconnected with an exterior surface of the anterior cutting guide portion 410 similar to the stylus 206 connected with the alignment guide 200, according to various embodiments.

In addition to or alternatively to the stylus 480, a removable claw or stylus member 490 may be provided or used. The removable stylus member 490 may have a bone contacting portion 492 and a ledge or finger 494 that is received within the slot 432 of the anterior cut guide portion 410. The claw 490 can be removably positioned within the slot 432 to allow for selective contact or orientation relative to the femur 80. Thus, the removable claw 490 may be quickly associated with the adjustable cut guide 400 for the adjustment portion of the procedure.

In other words, the foot 470 and the respective stylus 480 or claw 490 can assist in positioning the cut block 400 relative to the patient. Also, the cut block 400 may include an adjustment system 499 that includes an adjustment member 500 that is rotatable relative to a marking 502 on a housing portion 511 of the cut guide 400. The adjustment member 500 can include demarcations, such as numerals 510 to allow for selective positioning of the anterior cutting portion 410 and the posterior cutting portion 420. The adjustable member 500 can rotate to allow for aligning the respective markings 510 with the indices 502 on the cut guide 400 by rotating the adjustment member 500. It is understood that the numerals 510 may also be on the cut guide 400 on a housing portion 511 relative to which the adjustment member 500 may move. A single indicia, such as a line, on the adjustment member may then be moved relative to numerals on the housing 511.

Movement of the adjustment member may cause the cut guide portions can be moved relative to one another and/or relative to the chamfer cut guide portion 430 generally in the direction of arrow 520. It is understood that rotating the adjustment member 500 in a first direction, such as a clockwise direction, may move the posterior and anterior cutting portion nearer the chamfer cutting portion 430. Rotating the adjustment member 500 in a counterclockwise motion may move posterior and anterior cutting portion further from the chamfer cutting portion 430. It is understood, however, that any appropriate rotation could be used to move the respective cutting portions relative to each other. In addition, other mechanisms may be used to move the adjustment system or member 500. For example, motors may be driven based on instructions received from a transmitter. The instructions may be first processed with a processor provided with the guide 200 to move the motors and, thus, the adjustment. Also a key member may be formed that will move the adjustment member to a selected position. All of the adjustments may be based on the plan, as discussed above.

Figure 11:
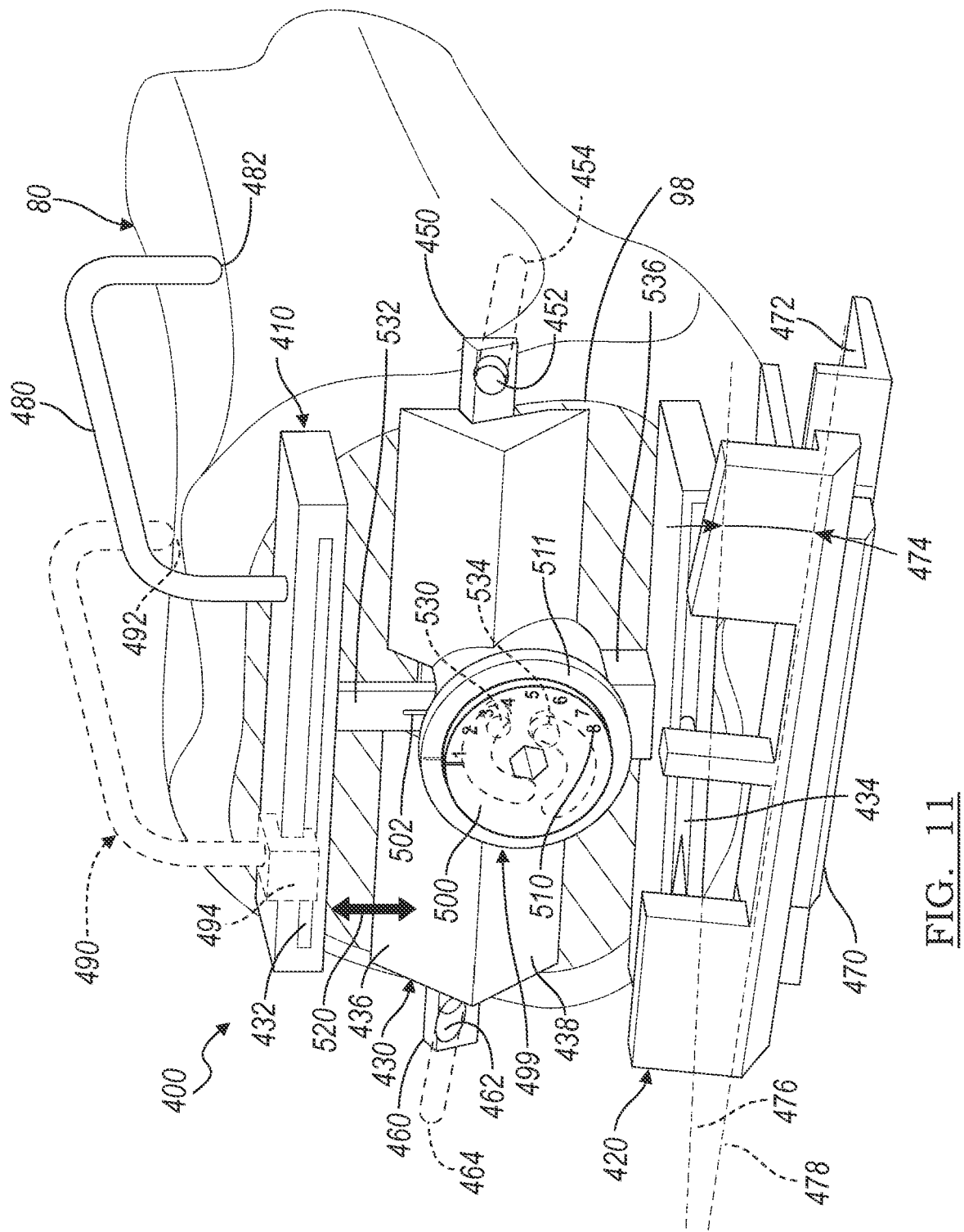
FIG. 11 is a front perspective environmental view of an adjustable cut guide system for a femur, according to various embodiments.

Further, the movement member 500 can operate by engaging at least a first pin 530 on a first holding member or riser 532 or a second pin 534 on a second holding member or riser 536. The first riser 532 may be moveably received within a slot or groove 533 of the second riser 536. With continuing reference to FIG. 11, the adjustment member 500 can include a first groove 540 and a second groove 542 formed into a surface 544 of the adjustment member 500. The first and second grooves 540, 542 can include different radii such that an adjustment of the first or second riser 532, 536 relative to the chamfer member 430 can be variable. For example, the anterior cutting portion 410 connected with the first riser 532 may be configured to move at a different rate relative to the chamfer member 430 then the chamfer member 430 relative to the posterior cutting portion 420. Further, even within one groove the rate could change to allow for a greater rate of movement during at least one portion of the rotation. Accordingly, engagement of the pin within the grooves 540, 542 can cause adjustment variability of the various members of the adjustable cut block 400.

Figure 12:
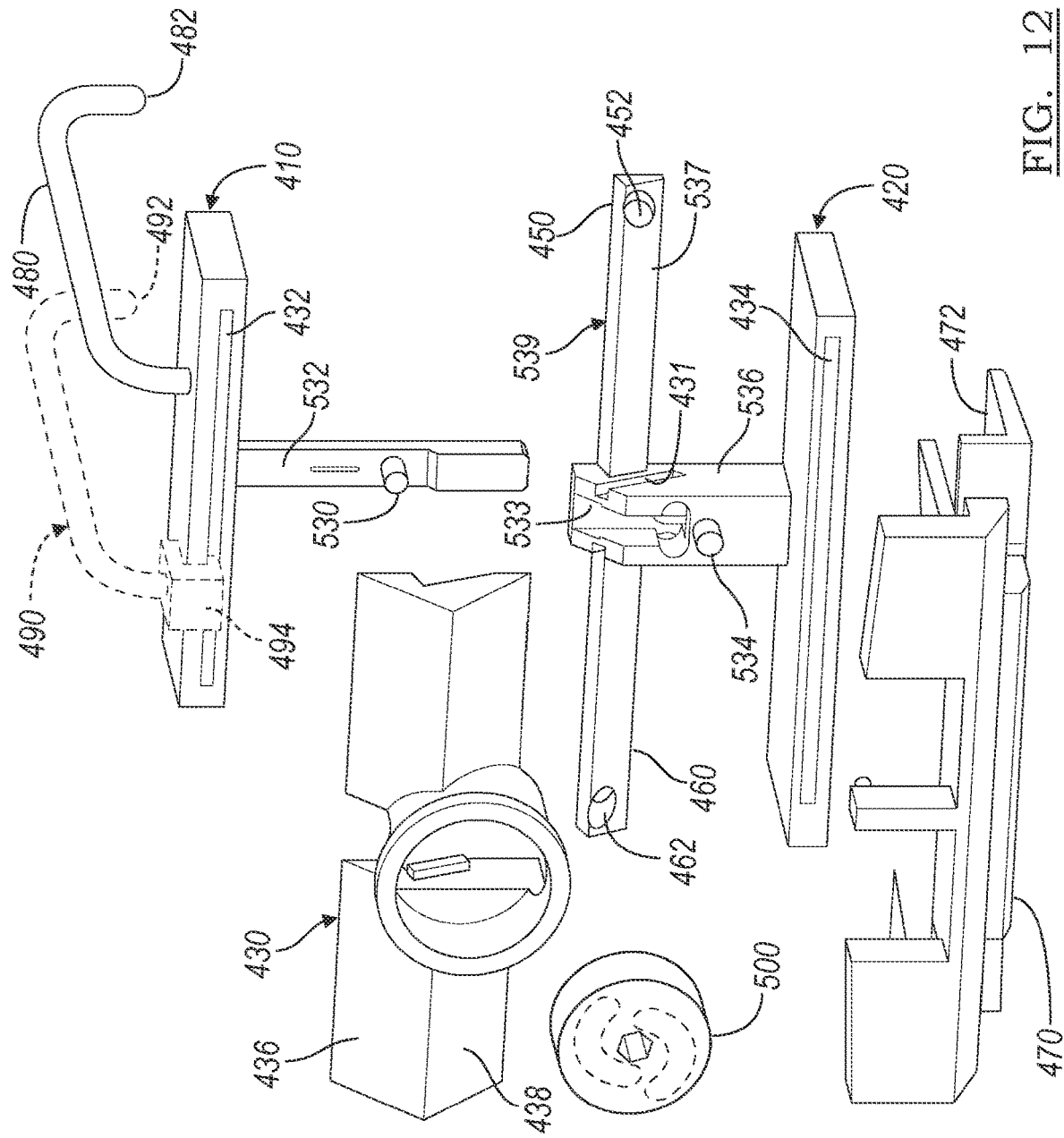
FIG. 12 is an exploded front perspective view of the adjustable cut guide system for a femur illustrated in FIG. 11.
Figure 13:
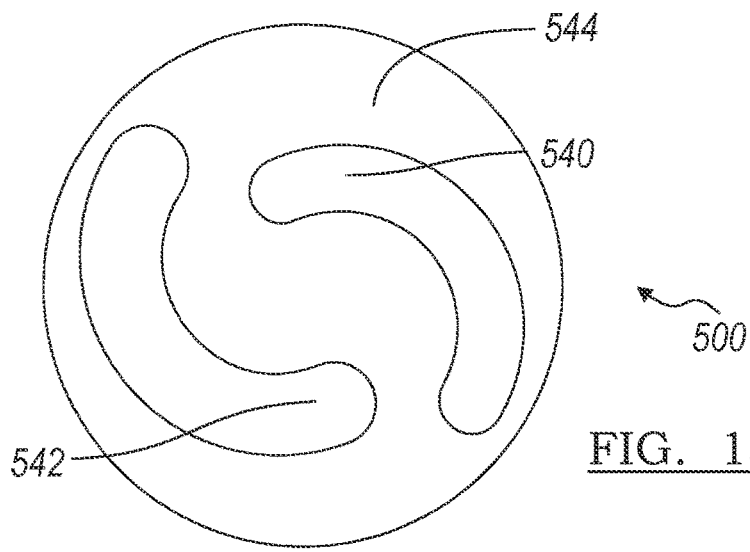
FIG. 13 is a detailed view of a second surface of a portion of the alignment system of FIG. 11.

In various embodiments, the portions of the guide 400 need not move parallel or in a single plane. For example, the chamfer guide member 430 may move at an angle or not parallel to a plane of the distal resected surface 98 of the femur 80. With reference to FIG. 12, the chamfer member 430 may move in the slot or groove 431. The groove 431 may be parallel with a surface 537 of a support bar 539 that extends from riser 536. The projections 450, 460 may also be formed as part of the support bar 539. The chamfer member 430, therefore, may move away or along a plane at an angle relative to the distal surface 98 to allow for more clearance in a chamfer resection. In other words, the movement of the various portions of the guide 400 may allow the guide portions 410, 420, and 430 to all move in selected and independent directions to achieve a desired or selected configuration of the guide 400. This allows for resecting the distal femur in a selected configuration to achieve a desired or planned resection for positioning a prosthesis thereon.

Nevertheless, according to various embodiments, the adjustable cut block 400 can be positioned relative to the distal femur 98 such that the posterior foot 470 engages a posterior side 96 of the femur and at least one of the stylus or claw 480, 490 engages an anterior side 94 of the femur and the adjustment member 500 is adjusted to the selected position such that each of the cutting portions, including the anterior cutting portion 410, the posterior cutting portion 420, and the chamfer cutting portion 430 are adjusted according to a predetermined position relative to the distal femur 98.

Once the adjustments of the adjustable block 400 have been made according to the plan, the projections 450, 460 can be used to visualize the orientation to the epicondylar axis. Also, engaging the cutting block 400 to the femur 80 with fixation pins, as noted above. The resections of the distal femur can then be made to prepare the anterior and posterior surfaces 94, 96 and chamfer surfaces for a distal femoral prosthesis. Appropriate distal femoral prostheses can include the Ascent™ knee system, sold by Biomet, Inc. having a place of business in Warsaw, Indiana.

The presently disclosed system's adjustability, including the adjustable cutting block 400, can minimize a supply of cutting blocks provided to a user and/or stored at a site due to the adjustability of the block 400. Further, based upon the planning, such as with the Signature® Planning System and/or the method 20, the adjustable block 400 can be provided at a more patient specific size. Thus, the adjustment required of the adjustable cut block 400 may be within a small range. The adjustability provided by the adjustable member 500 allows for any variation of the specific patient, which can be identified to the user via positioning the markings of the adjustable member 500 at a selected orientation relative to the indicia 502.

Accordingly, the femur 80 can be prepared for receipt of a distal femoral prosthesis using only the alignment guide, such as the alignment guide 200, and the adjustable cutting block 400. This can minimize or eliminate the use of the intramedullary rod 78 and/or additional instruments to size the sections of the distal femur 98. Thus, a procedure for preparing a distal femur can be performed efficiently and in a shorter period of time in conjunction with the planning system, such as the method 20 discussed above, used in conjunction with image data of a subject.

Figure 14:
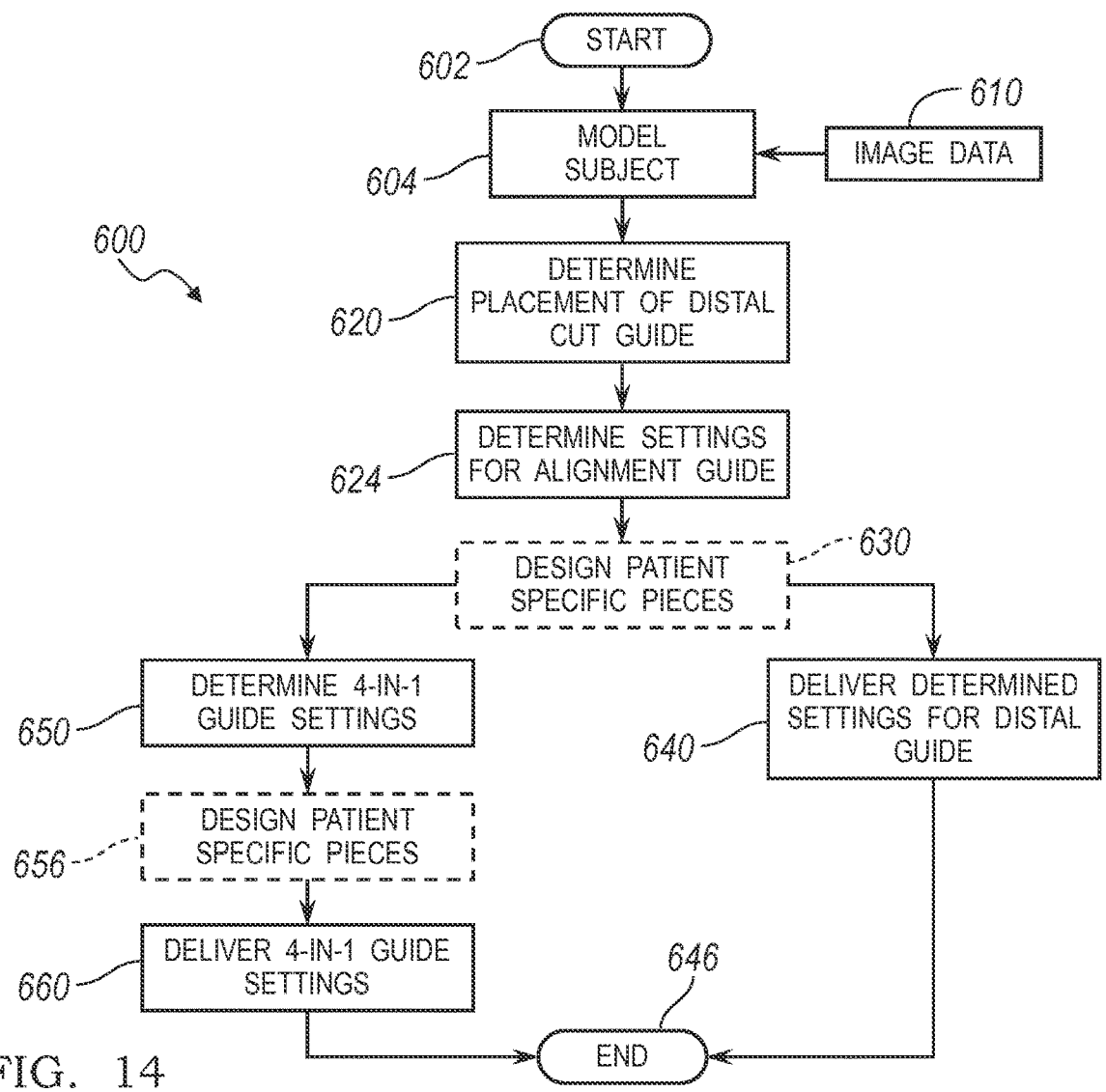
FIG. 14 is a flowchart illustrating a use of the system disclosed herein, according to various embodiments.

The various systems, including the distal alignment guides and/or adjustable cut guides discussed above may be used according to various methods and systems, including the method 600 illustrated in FIG. 14. Generally, the method can start at block 602 and a model of the subject may be made in block 604. The model of the subject can be a three dimensional model based upon various image data input from block 610. The image data can include image data such as MRI image data or Computed Tomography (CT) image data. Furthermore, two-dimensional image data can be rendered into three dimensions, such as based upon one or more two-dimensional x-rays acquired of a subject. It is understood that various subjects can include a human subject, animal subject, or other subject. Additionally, non-living subjects such as encased members (e.g., an automotive or aircraft fuselage or wing) may also be imaged and be modeled as the subject in block 604.

Based upon the model, a determination of placement of a distal cut guide, such as the distal guide 200 illustrated above, can be made in block 620. The determination of the placement of the distal cut guide can be based upon the various systems, such as the method 20 discussed above. The determination of placement of the cut guide can include where a cut guide should be positioned on a distal femur for performing a distal resection. Once it is determined where the cut guide should be positioned, determination of settings for the alignment guide can be made in a settings block 624.

The alignment guide can include the distal alignment guide 200, according to various embodiments, as discussed above. The determination of the settings for the alignment guide can include a determination of which setting to place the adjustment member to achieve an appropriate placement of the alignment member relative to the distal femur. As discussed above, the positioning of the alignment block can be used to position pins that are used to fix the cutting guide during a resection of the distal femur. If a patient-specific stylus 206 is to be designed, a patient-specific stylus may also be designed in block 630. The designing may include or be limited to selecting dimensions of the stylus 206. Further design, such as material selection and specific geometry may occur separately from the method 600. Other patient-specific designed pieces can also be made and/or designed based upon the plan and settings determined in block 624. It is understood that selected portions can be designed in addition to the stylus and the stylus is merely exemplary.

According to various embodiments, once the patient-specific pieces are designed and manufactured, if selected, it can be delivered along with the determined settings in block 640. The method may then end in block 646 if placement of the distal cut guide is the only selected purpose of the method. Even if other portions are selected, in positioning the distal guide with the distal alignment guide and determining settings of block 624 allows elimination of an IM rod and access to an intramedullary canal. Further, an angle guide, such as the angle guide included with the Ascent™ knee system, sold by Biomet, Inc. may be eliminated. Thus, the alignment guide and the determined settings can be delivered to a user, including a surgeon, to be the only system members to position the distal cut guide for making a distal resection of the femur.

Also, as discussed above, settings for an adjustable 4-in-1 cut block can be determined in block 650. The settings can be determined based upon the model of the subject from block 604 and using various planning systems such as the method 20 discussed above. The settings can be used to set the position of the movable member 500, as discussed above. Further, as also discussed above, patient-specific pieces can be designed and manufactured in block 656.

Once the settings are determined in block 650 and, if selected, patient-specific pieces are designed and manufactured in block 656, they may be delivered in block 660. The user may then use the settings, as discussed above, to perform a procedure and the method determined in block 646. By using the adjustable cut guide, and the settings related thereto, a generally known distal femoral sizer may not be necessary to size for a chamfer, anterior, and posterior cut guide for a distal femur. Rather, the settings can be predetermined and the adjustable cut guide can be adjusted based upon the determined settings.

According to the method illustrated in FIG. 14, and the various instruments and systems discussed above, a distal femoral resection and preparation can be performed with substantially only the distal alignment guide, distal cut guide, and the adjustable 4-in-1 cut block. This can achieve a fast procedure and may reduce inventory required for performing a procedure based upon selected instrument sets. Thus, one skilled in the art may be able to perform a procedure in a period of time beneficial to a patient and with reduced access to intramedullary portions of bone structures.

One skilled in the art will understand that the method, including the various embodiments illustrated in FIGS. 1 and/or 14 may be executed by developing appropriate algorithms and instructions (such as computer executable code) to perform the various steps. In addition, the determinations and decisions made may be based on various input instructions (such as the input result in block 30) and obtained data (such as the data from block 24 or the model in block 604). As noted above, the patient data may be anthropometric data that relates to size of a patient or subject including anterior-to-posterior dimensions, pelvic dimensions, etc. In various embodiments, therefore, settings for various instruments and the determination of the selection of instruments may be made on this data. For example, at least one determined instrument setting and the determined plan may both be based on at least one of determined axes in the obtained data, determined planes in the obtained data, identified axes in the obtained input, algorithmic analysis of the determined axes, theoretical motion analysis of the obtained data, accessing a database of the plurality of known instrument settings, accessing a database of known implant configurations. As discussed above, the user may input determined and/or identified axes. Further, selected tools (such as software tools) may be used to analyze the obtained data to determine planes of various objects (e.g. bones, soft tissue, support structures, structural walls) in the data. Also, known or developed instruments and prosthesis may have configurations (e.g. size, geometry, materials, size ranges) that are known and stored in databases that may be accessed by the selected systems. Again, the selected systems may have a general processor or a selected application specific circuit, as discussed above, to execute the instructions. In selected embodiments, visual recognition software may be used to visualize the femur 80 and the guide 200 to facilitate placement of the guide 200. In this case, options could be sensors that are installed on the femur 80 that orient in the field of view of a camera for use by the visual recognition software to position the guide 200.

It is understood that the plan, as discussed above, need not be limited to a distal femoral preparation. For example, in placing a proximal tibial prosthesis a plan and/or guides to achieve a plan may be useful to eliminate steps and/or ensure that a plan is achieved. During a procedure to implant a proximal tibial prosthesis, such as the proximal tibial prosthesis Vanguard XP Total Knee System, sold by Biomet, Inc. having a place of business in Warsaw, IN, a plan may be useful. According to various techniques, a boney island is maintained on a proximal surface of the tibia to maintain connection of an anterior cruciate ligament. Resection to form the boney island may be assisted with a plan, as discussed above, based on images of a subject, and selected guides or settings to guide resection of the tibia to form the boney island. Accordingly, it is understood that the plan as discussed above is not limited to any specific portion of an anatomy or to a human or animal subject.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

What is claimed is:

1. A computer-based system for selecting prostheses for an arthroplasty of a hip joint of a subject, the system comprising:
   one or more processors; and
   memory storing instructions that, when executed by the one or more processors, cause the one or more processors to perform operations, the operations comprising:
   receiving image data of a femur of the subject;
   storing the image data in a database in the computer-based system;
   identifying, on a touchscreen display, landmarks of the hip joint to identify a mechanical axis and a femoral axis of the femur;
   calculating a valgus angle between the mechanical axis and the femoral axis;
   calculating a possible range of motion of the femur;
   interactively determining, with a user or a surgeon, a final valgus angle that can be incorporated into a treatment plan;
   interactively determining, with the user or the surgeon, a desired post-implantation range of motion of the femur;
   determining a first range of appropriate sizes for an acetabular prosthesis;
   selecting a first size for the acetabular prosthesis from a first plurality of discrete sizes stored in the database, the first size being within the first range of appropriate sizes;
   determining a second range of appropriate sizes for a femoral head prosthesis;
   selecting a second size for the femoral head prosthesis from a second plurality of discrete sizes stored in the database, the second size being within the second range of appropriate sizes;
   determining a third range of appropriate sizes for a femoral stem prosthesis,
   selecting a third size for the femoral stem prosthesis from a third plurality of discrete sizes stored in the database, the third size being within the third range of appropriate sizes, the first, second, and third ranges of appropriate sizes configured to achieve the final valgus angle and the desired post-implantation range of motion of the femur;
   calculating a resulting valgus angle and a resulting range of motion of the femur based on the first size, the second size, and the third size;
   storing the resulting valgus angle and the resulting range of motion of the femur in the computer-based system as computed values of final valgus angle and post-implantation range of motion of the femur;
   determining that implantation in the subject of an acetabular prosthesis having the first size, implantation in the subject of a femoral head prosthesis having the second size, and implantation in the subject of a femoral stem prosthesis having the third size would achieve the final valgus angle and the desired post-implantation range of motion of the femur;
   displaying, on the touchscreen display, data representing the first size, the second size, and the third size;
   determining a position and an orientation of the femur relative to a pelvis of the subject to achieve the final valgus angle and the desired post-implantation range of motion of the femur, and
   displaying the determined position and the determined orientation of the femur relative to the pelvis on the touchscreen display.

2. The system of claim 1, wherein the image data includes at least one of:
   a three-dimensional magnetic resonance image of the femur,
   a three-dimensional computer tomography image of the femur, or
   a two-dimensional x-ray image of the femur.

3. The system of claim 2, wherein:
   the image data includes a selectable number of two-dimensional x-ray images of the femur, and
   the selectable number of two-dimensional x-ray images of the femur includes at least one of an anterior-to-posterior x-ray two-dimensional image or a medial-to-lateral two-dimensional x-ray image.

4. The system of claim 3, wherein the image data includes a plurality of two-dimensional x-ray images of the femur.

5. The system of claim 4, wherein the operations further comprise:
   generating a three-dimensional reconstruction of the femur based on the plurality of two-dimensional x-ray images of the femur.

6. The system of claim 5, wherein the operations further comprise:
   displaying a visual illustration of the three-dimensional reconstruction of the femur on the touchscreen display,
   wherein data representing the desired post-implantation range of motion of the femur are superimposed on the visual illustration of the three-dimensional reconstruction of the femur.

7. The system of claim 5, wherein the operations further comprise:
   based on the three-dimensional reconstruction of the femur, automatically selecting at least one of the first size, the second size, or the third size.

8. The system of claim 2, wherein the operations further comprise:
   obtaining the two-dimensional x-ray images from a fluoroscopy system.

9. A computer-implemented method for selecting prostheses for an arthroplasty of a hip joint of a subject, the method comprising:
   receiving image data of a femur of the subject;
   storing the image data in a database in a computer;
   identifying, on a touchscreen display, landmarks of the hip joint to identify a mechanical axis and a femoral axis of the femur;
   calculating a valgus angle between the mechanical axis and the femoral axis;
   calculating a possible range of motion of the femur;
   interactively determining, with a user or a surgeon, a final valgus angle that can be incorporated into a treatment plan;
   interactively determining, with the user or the surgeon, a desired post-implantation range of motion of the femur;
   determining a first range of appropriate sizes for an acetabular prosthesis;
   selecting a first size for the acetabular prosthesis from a first plurality of discrete sizes stored in the database, the first size being within the first range of appropriate sizes;
   determining a second range of appropriate sizes for a femoral head prosthesis;

selecting a second size for the femoral head prosthesis from a second plurality of discrete sizes stored in the database, the second size being within the second range of appropriate sizes;

determining a third range of appropriate sizes for a femoral stem prosthesis, selecting a third size for the femoral stem prosthesis from a third plurality of discrete sizes stored in the database, the third size being within the third range of appropriate sizes, the first, second, and third ranges of appropriate sizes configured to achieve the final valgus angle and the desired post-implantation range of motion of the femur;

calculating a resulting valgus angle and a resulting range of motion of the femur based on the first size, the second size, and the third size;

storing the resulting valgus angle and the resulting range of motion of the femur in the computer as computed values of final valgus angle and post-implantation range of motion of the femur;

determining that implantation in the subject of an acetabular prosthesis having the first size, implantation in the subject of a femoral head prosthesis having the second size, and implantation in the subject of a femoral stem prosthesis having the third size would achieve the final valgus angle and the desired post-implantation range of motion of the femur;

displaying, on the touchscreen display, data representing the first size, the second size, and the third size;

determining a position and an orientation of the femur relative to a pelvis of the subject to achieve the final valgus angle and the desired post-implantation range of motion of the femur; and displaying the determined position and the determined orientation of the femur relative to the pelvis on the touchscreen display.

10. The method of claim 9, wherein the image data includes at least one of:
   a three-dimensional magnetic resonance image of the femur,
   a three-dimensional computer tomography image of the femur, or
   a two-dimensional x-ray image of the femur.

11. The method of claim 10, wherein:
   the image data includes a selectable number of two-dimensional x-ray images of the femur, and
   the selectable number of two-dimensional x-ray images of the femur includes at least one of an anterior-to-posterior x-ray two-dimensional image or a medial-to-lateral two-dimensional x-ray image.

12. The method of claim 11, wherein the image data includes a plurality of two-dimensional x-ray images of the femur.

13. The method of claim 12, further comprising:
   generating a three-dimensional reconstruction of the femur based on the plurality of two-dimensional x-ray images of the femur.

14. The method of claim 13, further comprising:
   displaying a visual illustration of the three-dimensional reconstruction of the femur on the touchscreen display, wherein data representing the desired post-implantation range of motion of the femur are superimposed on the visual illustration of the three-dimensional reconstruction of the femur.

15. The method of claim 13, further comprising:
   based on the three-dimensional reconstruction of the femur, automatically selecting at least one of the first size, the second size, or the third size.

16. The method of claim 10, further comprising:
   obtaining the two-dimensional x-ray images from a fluoroscopy system.

* * * * *

UNITED STATES PATENT AND TRADEMARK OFFICE
CERTIFICATE OF CORRECTION

| | | |
|---|---|---|
| PATENT NO. | : 12,096,989 B2 | Page 1 of 1 |
| APPLICATION NO. | : 17/490146 | |
| DATED | : September 24, 2024 | |
| INVENTOR(S) | : Brown et al. | |

It is certified that error appears in the above-identified patent and that said Letters Patent is hereby corrected as shown below:

On the Title Page

On page 2, in Column 2, item (56) under "Other Publications", Line 28, delete "malled" and insert --mailed-- therefor In the Claims In Column 23, Line 67, in Claim 1, delete "femur," and insert --femur;-- therefor Signed and Sealed this
Tenth Day of December, 2024

Katherine Kelly Vidal
*Director of the United States Patent and Trademark Office*